United States Patent
Domon et al.

(10) Patent No.: US 9,285,678 B2
(45) Date of Patent: Mar. 15, 2016

(54) SULFONIUM SALT, RESIST COMPOSITION AND RESIST PATTERN FORMING PROCESS

(71) Applicant: SHIN-ETSU CHEMICAL CO., LTD., Tokyo (JP)

(72) Inventors: Daisuke Domon, Joetsu (JP); Keiichi Masunaga, Joetsu (JP); Masayoshi Sagehashi, Joetsu (JP); Satoshi Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/567,061

(22) Filed: Dec. 11, 2014

(65) Prior Publication Data
US 2015/0168829 A1 Jun. 18, 2015

(30) Foreign Application Priority Data
Dec. 18, 2013 (JP) ................................. 2013-261348

(51) Int. Cl.
| | | |
|---|---|---|
| G03F 7/004 | (2006.01) | |
| G03F 7/039 | (2006.01) | |
| G03F 7/20 | (2006.01) | |
| G03F 7/30 | (2006.01) | |
| G03F 7/32 | (2006.01) | |
| C07C 381/12 | (2006.01) | |
| C07C 309/04 | (2006.01) | |
| C07C 309/07 | (2006.01) | |
| C07C 309/29 | (2006.01) | |
| C07C 309/30 | (2006.01) | |
| C07C 309/31 | (2006.01) | |
| C07C 309/35 | (2006.01) | |
| C07C 309/42 | (2006.01) | |
| C07C 309/43 | (2006.01) | |
| G03F 1/00 | (2012.01) | |

(52) U.S. Cl.
CPC ............ *G03F 7/0045* (2013.01); *C07C 309/04* (2013.01); *C07C 309/07* (2013.01); *C07C 309/29* (2013.01); *C07C 309/30* (2013.01); *C07C 309/31* (2013.01); *C07C 309/35* (2013.01); *C07C 309/42* (2013.01); *C07C 309/43* (2013.01); *C07C 381/12* (2013.01); *G03F 7/0392* (2013.01); *G03F 7/0397* (2013.01); *G03F 7/2041* (2013.01); *G03F 7/30* (2013.01); *G03F 7/322* (2013.01); *G03F 1/08* (2013.01)

(58) Field of Classification Search
None
See application file for complete search history.

(56) References Cited

U.S. PATENT DOCUMENTS

| | | | |
|---|---|---|---|
| 6,280,898 B1 | 8/2001 | Hasegawa et al. | |
| 7,527,912 B2 | 5/2009 | Ohsawa et al. | |
| 7,537,880 B2 | 5/2009 | Harada et al. | |
| 7,678,530 B2 | 3/2010 | Hasegawa et al. | |
| 7,977,027 B2 | 7/2011 | Takeda et al. | |
| 8,343,694 B2 | 1/2013 | Koitabashi et al. | |
| 8,361,693 B2 | 1/2013 | Masunaga et al. | |
| 8,703,384 B2 * | 4/2014 | Kobayashi et al. | 430/270.1 |
| 8,835,097 B2 * | 9/2014 | Domon et al. | 430/270.1 |
| 2004/0260031 A1 | 12/2004 | Takeda et al. | |
| 2009/0202947 A1* | 8/2009 | Hatakeyama et al. | 430/287.1 |
| 2010/0316952 A1* | 12/2010 | Ichikawa et al. | 430/270.1 |
| 2011/0117493 A1 | 5/2011 | Ichikawa et al. | |
| 2011/0171577 A1 | 7/2011 | Tsuchimura et al. | |
| 2011/0294070 A1* | 12/2011 | Hatakeyama et al. | 430/285.1 |
| 2012/0135350 A1* | 5/2012 | Kobayashi et al. | 430/285.1 |
| 2012/0308920 A1* | 12/2012 | Domon et al. | 430/5 |
| 2012/0308932 A1* | 12/2012 | Sagehashi et al. | 430/285.1 |

FOREIGN PATENT DOCUMENTS

| | | |
|---|---|---|
| JP | 2000-159758 A | 6/2000 |
| JP | 2004-115630 A | 4/2004 |
| JP | 2005-8766 A | 1/2005 |
| JP | 2007-182488 A | 7/2007 |
| JP | 2008-102383 A | 5/2008 |
| JP | 2008-111103 A | 5/2008 |
| JP | 2008-304590 A | 12/2008 |
| JP | 2009-53518 A | 3/2009 |
| JP | 2010-100604 A | 5/2010 |
| JP | 2011-22564 A | 2/2011 |
| JP | 5083528 B2 | 11/2012 |
| TW | 201129552 A | 9/2011 |
| TW | 201307273 A | 2/2013 |
| WO | 2006/121096 A1 | 11/2006 |

OTHER PUBLICATIONS

Office Action dated Jul. 6, 2015, issued in counterpart Taiwanese Patent Application No. 103143751 (4 pages).

* cited by examiner

*Primary Examiner* — Sin Lee
(74) *Attorney, Agent, or Firm* — Westerman, Hattori, Daniels & Adrian, LLP

(57) ABSTRACT

A sulfonium salt of formula (1) is provided wherein $A^1$ is a divalent hydrocarbon group, $A^2$ is a divalent hydrocarbon group, $A^3$ is hydrogen or a monovalent hydrocarbon group, $B^1$ is an alkylene or arylene group, k is 0 or 1, $R^1$, $R^2$ and $R^3$ are alkyl, alkenyl, oxoalkyl, aryl, aralkyl or aryloxoalkyl. A resist composition comprising the sulfonium salt as PAG exhibits a very high resolution when processed by EB and EUV lithography. A pattern with minimal LER is obtainable.

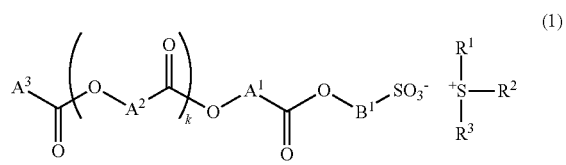

(1)

11 Claims, No Drawings

SULFONIUM SALT, RESIST COMPOSITION AND RESIST PATTERN FORMING PROCESS

CROSS-REFERENCE TO RELATED APPLICATION

This non-provisional application claims priority under 35 U.S.C. §119(a) on Patent Application No. 2013-261348 filed in Japan on Dec. 18, 2013, the entire contents of which are hereby incorporated by reference.

TECHNICAL FIELD

This invention relates to a sulfonium salt, a chemically amplified resist composition, and a resist pattern forming process. The chemically amplified, typically positive, resist composition is sensitive to high-energy radiation such as UV, deep-UV, EUV, X-ray, γ-ray, synchrotron radiation, and EB, and especially suited for use in the exposure step of irradiating high-energy radiation, typically EB, EUV or deep-UV, and adapted for microfabrication of semiconductor devices and photomasks.

BACKGROUND ART

To meet the recent demand for higher integration in integrated circuits, pattern formation to a finer feature size is required. Acid-catalyzed chemically amplified resist compositions are most often used in forming resist patterns with a feature size of 0.2 μm or less. High-energy radiation such as UV, deep-UV or electron beam (EB) is used as the light source for exposure of these resist compositions. In particular, while EB lithography is utilized as the ultra-fine microfabrication technique, it is also indispensable in processing a photomask blank to form a photomask for use in semiconductor device fabrication.

In general, the EB lithography is by writing an image with EB, without using a mask. In the case of positive resist, those regions of a resist film other than the regions to be retained are successively irradiated with EB having a minute area. The operation of successively scanning all finely divided regions on the work surface takes a long time as compared with full wafer exposure through a photomask. In order to avoid any decline of throughput, the resist film must be highly sensitive. Because of the long image-writing time, there is a likelihood of a difference arising between the initially written portion and the later written portion. Thus the stability with time of exposed regions in vacuum is one of important performance requirements. One of the important applications of chemically amplified resist material resides in processing of photomask blanks. Some photomask blanks have a surface material that can have an impact on the pattern profile of the overlying chemically amplified resist film, such as a layer of a chromium compound, typically chromium oxide deposited on a photomask substrate. For high resolution and profile retention after etching, it is one important performance factor to maintain the pattern profile of resist film rectangular independent of the type of substrate.

The control of resist sensitivity and pattern profile as mentioned above has been improved by a proper selection and combination of resist material-constituting components and processing conditions. One outstanding improvement is directed to the diffusion of acid that largely affects the resolution of a chemically amplified resist film. In processing of photomasks, it is required that the profile of a resist pattern formed as above do not change with a lapse of time from the end of exposure to PEB. The major cause of such a change with time is diffusion of an acid generated upon exposure. The problem of acid diffusion has been widely studied not only in the field of photomask processing, but also in the field of general resist films because it has a significant impact on sensitivity and resolution.

Patent Documents 1 and 2 describe acid generators capable of generating bulky acids for controlling acid diffusion and reducing roughness. Since these acid generators are still insufficient in control of acid diffusion, it is desired to have an acid generator with more controlled diffusion.

Patent Document 3 discloses a resist composition comprising a base resin to which a sulfonic acid generated upon light exposure is bound so that the acid diffusion is controlled. This approach of controlling acid diffusion by binding recurring units capable of generating acid upon exposure to a base polymer is effective in forming a pattern with minimal LER. However, a problem arises with respect to the solubility in organic solvent of the base polymer having bound therein recurring units capable of generating acid upon exposure, depending on the structure and proportion of such recurring units.

Polymers comprising a major proportion of aromatic structure having an acidic side chain, for example, polyhydroxystyrene have been widely used in resist materials for the KrF excimer laser lithography. These polymers are not used in resist materials for the ArF excimer laser lithography since they exhibit strong absorption at a wavelength of around 200 nm. These polymers, however, are expected to form useful resist materials for the EB and EUV lithography for forming patterns of finer size than the processing limit of ArF excimer laser because they offer high etching resistance.

Often used as the base polymer in positive resist compositions for EB and EUV lithography is a polymer having an acidic functional group on phenol side chain masked with an acid labile protective group wherein the acid labile protective group is deprotected by the catalysis of an acid generated from a photoacid generator upon exposure to high-energy radiation so that the polymer may become soluble in alkaline developer. Typical of the acid labile protective group are tertiary alkyl, tert-butoxycarbonyl, and acetal groups. On use of protective groups requiring a relatively low level of activation energy for deprotection such as acetal groups, a resist film having a high sensitivity is advantageously obtainable. However, if the diffusion of generated acid is not fully controlled, deprotection reaction can occur even in the unexposed regions of the resist film, giving rise to problems like degradation of line edge roughness (LER) and a lowering of in-plane uniformity of pattern line width (CDU).

Patent Document 4 describes a resist composition comprising a resin comprising recurring units having an acetal group and a sulfonium salt capable of generating an acid having a high pKa such as fluoroalkanesulfonic acid. Regrettably, the pattern obtained therefrom has substantial LER. This is because the acid strength of fluoroalkanesulfonic acid is too high for the deprotection of an acetal group requiring a relatively low level of activation energy for deprotection. So, even if acid diffusion is controlled, deprotection reaction can occur in the unexposed region with a minor amount of acid diffused thereto.

CITATION LIST

Patent Document 1: JP-A 2009-053518
Patent Document 2: JP-A 2010-100604
Patent Document 3: JP-A 2011-022564
Patent Document 4: JP 5083528

DISCLOSURE OF INVENTION

An object of the invention is to provide a sulfonium salt capable of generating an acid having an appropriate strength and controlled diffusion, a resist composition, specifically chemically amplified resist composition, and a resist pattern forming process.

The inventors have found that a sulfonium salt having the general formula (1) below generates an acid which is bulky and controlled in diffusion, and that a pattern with minimal LER is obtainable from a resist composition comprising the sulfonium salt.

In one aspect, the invention provides a sulfonium salt having the general formula (1).

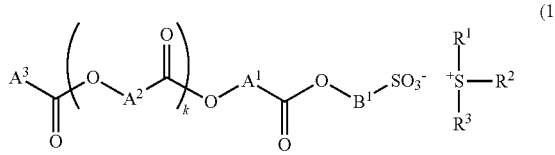

(1)

Herein $A^1$ is a straight, branched or cyclic, $C_1$-$C_{10}$ divalent hydrocarbon group which may be substituted with a heteroatom or separated by a heteroatom, $A^2$ is a straight, branched or cyclic, $C_1$-$C_{10}$ divalent hydrocarbon group, $A^3$ is hydrogen or a straight, branched or cyclic, $C_1$-$C_{30}$ monovalent hydrocarbon group which may be substituted with a heteroatom or separated by a heteroatom, $B^1$ is a $C_1$-$C_{10}$ alkylene group or $C_6$-$C_{18}$ arylene group which may contain an ethereal oxygen atom, k is 0 or 1, $R^1$, $R^2$ and $R^3$ are each independently a substituted or unsubstituted, straight or branched $C_1$-$C_{10}$ alkyl, alkenyl or oxoalkyl group, or a substituted or unsubstituted $C_6$-$C_{18}$ aryl, aralkyl or aryloxyalkyl group, or any two or more of $R^1$, $R^2$ and $R^3$ may bond together to form a ring with the sulfur atom.

Preferably, $A^1$ is a group having the general formula (2):

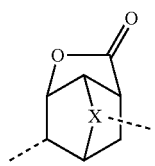

(2)

wherein X is O or $CH_2$, and the broken line denotes a valence bond.

Preferably, $A^3$ is a group having the general formula (3):

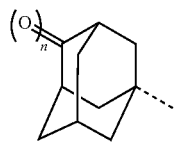

(3)

wherein n is 0 or 1, formula (3) denotes adamantyl when n=0, and the broken line denotes a valence bond.

In another aspect, the invention provides a resist composition comprising the sulfonium salt defined above. Typically, the resist composition further comprises a resin adapted to be decomposed under the action of acid to increase its solubility in alkaline developer.

In a preferred embodiment, the resin is a polymer comprising recurring units having the general formula (4).

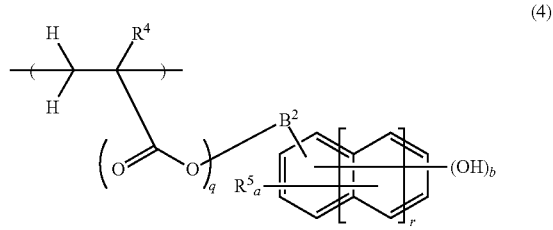

(4)

Herein q is 0 or 1, r is an integer of 0 to 2, $R^4$ is hydrogen, fluorine, methyl or trifluoromethyl, $R^5$ is each independently hydrogen or $C_1$-$C_6$ alkyl group, $B^2$ is a single bond or a $C_1$-$C_{10}$ alkylene group which may contain an ether bond, a is an integer satisfying a≤5+2r−b, and b is an integer of 1 to 3.

Preferably, the polymer may further comprise as an acid labile group-protected unit which turns alkali soluble under the action of acid, recurring units having the general formula (5).

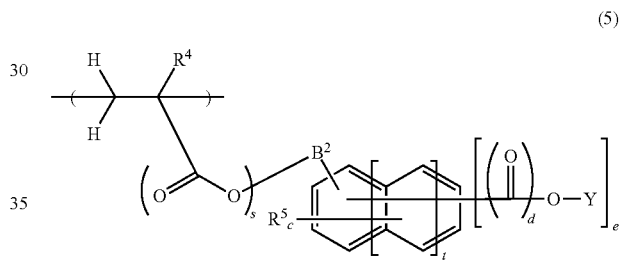

(5)

Herein s is 0 or 1, t is an integer of 0 to 2, $R^4$ and $R^5$ are as defined above, $B^3$ is a single bond or a $C_1$-$C_{10}$ alkylene group which may contain an ether bond, c is an integer satisfying c≤5+2t−e, d is 0 or 1, e is an integer of 1 to 3, Y is an acid labile group when e=1, Y is hydrogen or an acid labile group when e=2 or 3, with at least one Y being an acid labile group.

Preferably, the polymer may further comprise recurring units having the general formula (6) and/or (7).

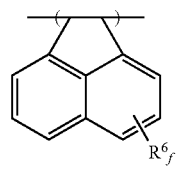

(6)

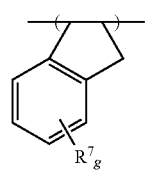

(7)

Herein f is an integer of 0 to 6, $R^6$ is each independently hydrogen, an optionally halo-substituted $C_1-C_6$ alkyl or primary or secondary alkoxy group, or optionally halo-substituted $C_1-C_7$ alkylcarbonyloxy group, g is an integer of 0 to 4, and $R^7$ is each independently hydrogen, an optionally halo-substituted $C_1-C_6$ alkyl or primary or secondary alkoxy group, or optionally halo-substituted $C_1-C_7$ alkylcarbonyloxy group.

In a further aspect, the invention provides a pattern forming process comprising the steps of applying the resist composition defined above onto a processable substrate to form a resist film, exposing the resist film to high-energy radiation, and developing in an alkaline developer to form a resist pattern.

The high-energy radiation is typically EUV or EB. The processable substrate may have an outermost surface made of a chromium-containing material. Typically, the processable substrate is a photomask blank.

Advantageous Effects of Invention

A resist composition comprising the sulfonium salt defined herein as PAG exhibits a very high resolution when processed by the micropatterning lithography, especially EB and EUV lithography. A pattern with minimal LER is obtainable therefrom.

DESCRIPTION OF PREFERRED EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. The term "film" is used interchangeably with "coating" or "layer." The term "processable layer" is interchangeable with patternable layer and refers to a layer that can be processed such as by etching to form a pattern therein.

The abbreviations and acronyms have the following meaning.

PAG: photoacid generator
Mw: weight average molecular weight
Mn: number average molecular weight
Mw/Mn: molecular weight distribution or dispersity
GPC: gel permeation chromatography
PEB: post-exposure baking
PED: post-exposure delay
LER: line edge roughness
CDU: critical dimension uniformity It is understood that for some structures represented by chemical formulae, there can exist enantiomers and diastereomers because of the presence of asymmetric carbon atoms. In such a case, a single formula collectively represents all such isomers. The isomers may be used alone or in admixture. In chemical formulae, the broken line denotes a valence bond.

Sulfonium Salt

One embodiment of the invention is a sulfonium salt having the general formula (1).

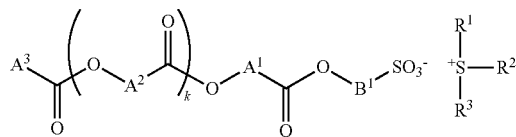

(1)

Herein $A^1$ is a straight, branched or cyclic, $C_1-C_{10}$ divalent hydrocarbon group which may be substituted with a heteroatom or separated by a heteroatom; $A^2$ is a straight, branched or cyclic, $C_1-C_{10}$ divalent hydrocarbon group; $A^3$ is hydrogen or a straight, branched or cyclic, $C_1-C_{30}$ monovalent hydrocarbon group which may be substituted with a heteroatom or separated by a heteroatom; $B^1$ is a $C_1-C_{10}$ alkylene group or $C_6-C_{18}$ arylene group which may contain an ethereal oxygen atom; k is 0 or 1; $R^1$, $R^2$ and $R^3$ are each independently a substituted or unsubstituted, straight or branched $C_1-C_{10}$ alkyl, alkenyl or oxoalkyl group, or a substituted or unsubstituted $C_6-C_{18}$ aryl, aralkyl or aryloxoalkyl group, or any two or more of $R^1$, $R^2$ and $R^3$ may bond together to form a ring with the sulfur atom.

In formula (1), $B^1$ is a $C_1-C_{10}$ alkylene group or a $C_6-C_{18}$ arylene group which may contain an ethereal oxygen atom. Examples of the alkylene and arylene groups are shown below, but not limited thereto.

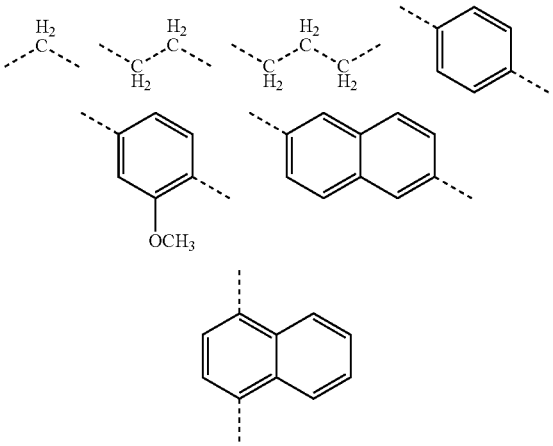

$A^2$ is a straight, branched or cyclic, $C_1-C_{10}$ divalent hydrocarbon group, examples of which are shown below, but not limited thereto.

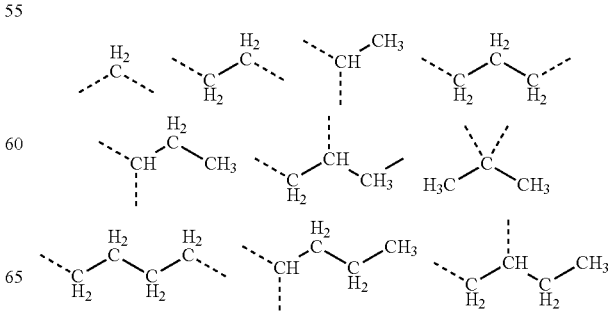

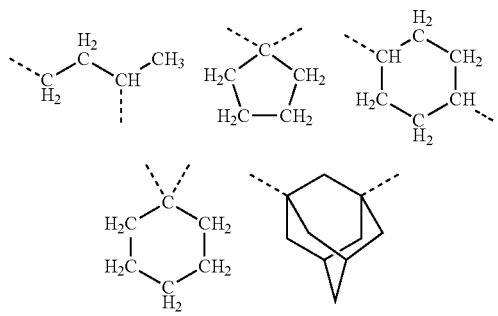

$A^1$ is a straight, branched or cyclic, $C_1$-$C_{10}$ divalent hydrocarbon group which may be substituted with a heteroatom or separated by a heteroatom, examples of which are shown below, but not limited thereto.

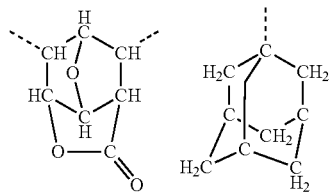

$A^3$ is hydrogen or a straight, branched or cyclic, $C_1$-$C_{30}$ monovalent hydrocarbon group which may be substituted with a heteroatom or separated by a heteroatom. Examples of the hydrocarbon group include such as methyl, ethyl, propyl, isopropyl, n-butyl, sec-butyl, tert-butyl, tert-amyl, n-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl. Also included are modified forms of the foregoing in which one or more hydrogen atoms are substituted by a heteroatom or atoms such as oxygen, sulfur, nitrogen or halogen, or a heteroatom or atoms such as oxygen, sulfur, nitrogen or halogen intervene, to form a hydroxyl, cyano, carbonyl, ether bond, ester bond, sulfonic acid ester bond, carbonate bond, lactone ring, sultone ring, carboxylic anhydride or haloalkyl.

Preferred structures of $A^3$ are exemplified below, but not limited thereto.

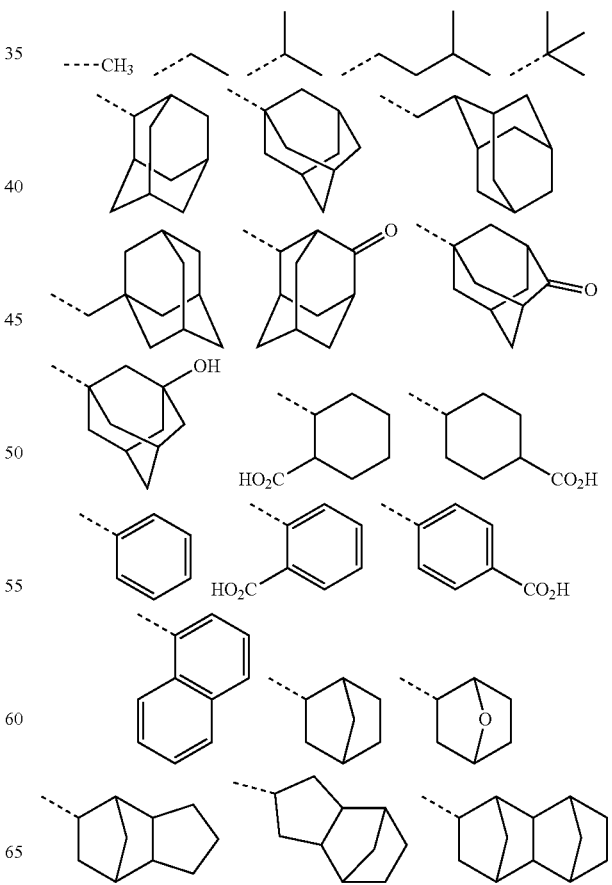

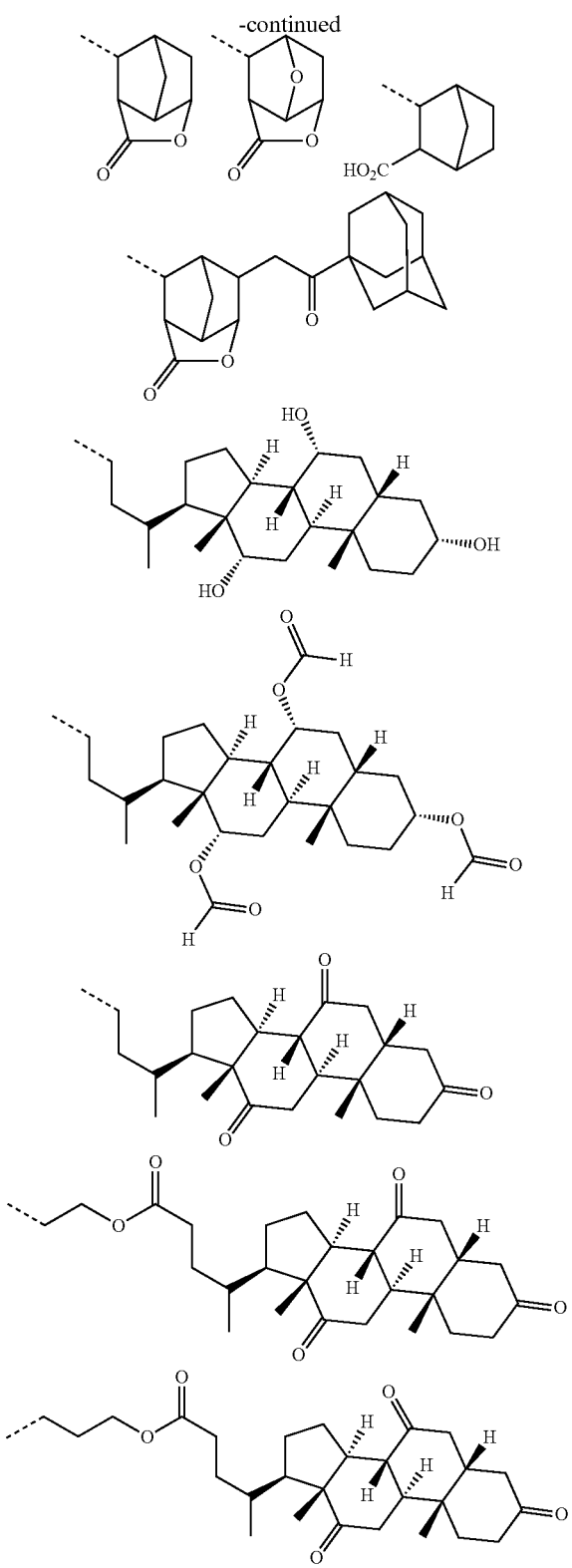

In formula (1), $R^1$, $R^2$ and $R^3$ are each independently a substituted or unsubstituted, straight or branched $C_1$-$C_{10}$ alkyl, alkenyl or oxoalkyl group, or a substituted or unsubstituted $C_6$-$C_{18}$ aryl, aralkyl or aryloxoalkyl group. Alternatively, at least two of $R^1$, $R^2$ and $R^3$ may bond together to form a ring with the sulfur atom in the formula.

Of the groups represented by $R^1$ to $R^3$, suitable alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl.

Suitable aryl groups include phenyl, naphthyl and thienyl, as well as hydroxyphenyl and alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, alkylnaphthyl groups such as methylnaphthyl and ethylnaphthyl, alkoxynaphthyl groups such as methoxynaphthyl and ethoxynaphthyl, dialkylnaphthyl groups such as dimethylnaphthyl and diethylnaphthyl, and dialkoxynaphthyl groups such as dimethoxynaphthyl and diethoxynaphthyl. Suitable aralkyl groups include benzyl, 1-phenylethyl, and 2-phenylethyl. Suitable aryloxoalkyl groups are 2-aryl-2-oxoethyl groups including 2-phenyl-2-oxoethyl, 2-(1-naphthyl)-2-oxoethyl, and 2-(2-naphthyl)-2-oxoethyl. Also included are aryl groups having a polymerizable substituent such as acryloyloxy or methacryloyloxy, for example, 4-acryloyloxyphenyl, 4-methacryloyloxyphenyl, 4-acryloyloxy-3,5-dimethylphenyl, 4-methacryloyloxy-3,5-dimethylphenyl, 4-vinyloxyphenyl, and 4-vinylphenyl.

Alternatively, at least two of $R^1$, $R^2$ and $R^3$ bond together to form a ring with the sulfur atom in the formula. Exemplary ring structure-forming groups include divalent organic groups such as 1,4-butylene and 3-oxa-1,5-pentylene.

Examples of the sulfonium cation include, but are not limited to, triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 5-phenyldibenzothiophenium, 10-phenylphenoxathiinium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. Of these, triphenylsulfonium, 4-tert-butylphenyldiphenylsulfonium, 4-tert-butoxyphenyldiphenylsulfonium, and tris(4-tert-butylphenyl)sulfonium are more preferred.

Also included are 4-methacryloyloxyphenyldiphenylsulfonium, 4-acryloyloxyphenyldiphenylsulfonium, 4-methacryloyloxyphenyldimethylsulfonium, 4-acryloyloxyphenyldimethylsulfonium, (4-methacryloyloxy-3,5-dimethylphenyl)diphenylsulfonium, and (4-acryloyloxy-3,5-dimethylphenyl)diphenylsulfonium.

Other examples of the sulfonium cation include 4-methylphenyldiphenylsulfonium, 4-ethylphenyldiphenylsulfonium, 4-tert-butylphenyldiphenylsulfonium, 4-cyclohexylphenyldiphenylsulfonium, 4-n-hexylphenyldiphenylsulfonium, 4-n-octylphenyldiphenylsulfonium, 4-methoxyphenyldiphenylsulfonium, 4-ethoxyphenyldiphenylsulfonium, 4-tert-butoxyphenyldiphenylsulfonium, 4-cyclohexyloxyphenyldiphenylsulfonium, 4-n-hexyloxyphenyldiphenylsulfonium, 4-n-octyloxyphenyldiphenylsulfonium, 4-dodecyloxyphenyldiphenylsulfonium, 4-trifluoromethylphenyldiphenylsulfonium, 4-trifluoromethyloxyphenyldiphenylsulfonium, 4-tert-butoxycarbonylmethyloxyphenyldiphenylsulfonium, 4-methacryloyloxyphenyldiphenylsulfonium, 4-acryloyloxyphenyldiphenylsulfonium, (4-n-hexyloxy-3,5-dimethylphenyl)diphenylsulfonium, (4-methacryloyloxy-3,5-dimethylphenyl)diphenylsulfonium, and (4-acryloyloxy-3,5-dimethylphenyl)diphenylsulfonium.

The preferred structure of $A^1$ in formula (1) is a structure having the general formula (2):

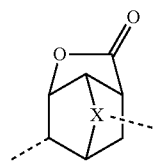

(2)

wherein X is O or $CH_2$,

Since the lactone structure of formula (2) is a polar group, the acid generated therefrom upon exposure effectively interacts with a phenolic hydroxyl-containing unit in a base resin to interrupt acid diffusion. The lactone structure eventually contributes to formation of a pattern with minimal roughness.

The preferred structure of $A^3$ in formula (1) is a structure having the general formula (3):

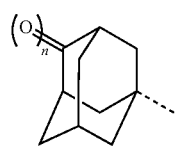

(3)

wherein n is 0 or 1. Formula (3) denotes adamantyl when n=0.

The structure of formula (3) is effective for suppressing the diffusion of acid generated upon exposure and eventually contributes to formation of a pattern with minimal roughness.

Preferred examples of the sulfonic acid anion in formula (1) are shown below.

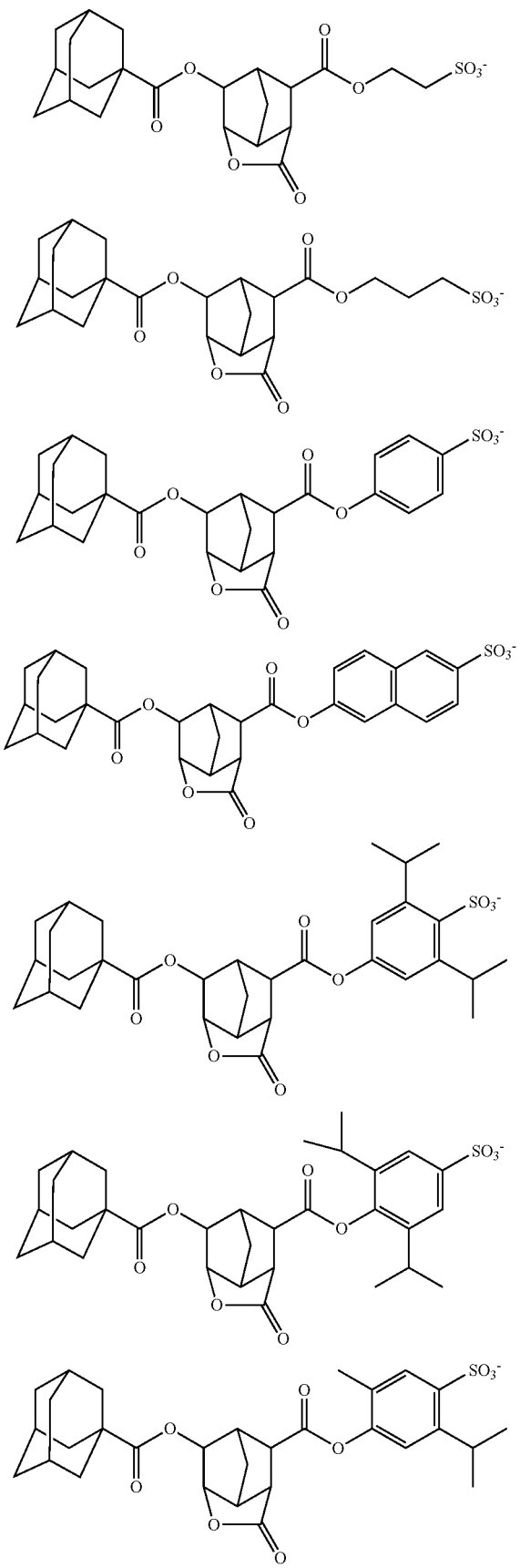

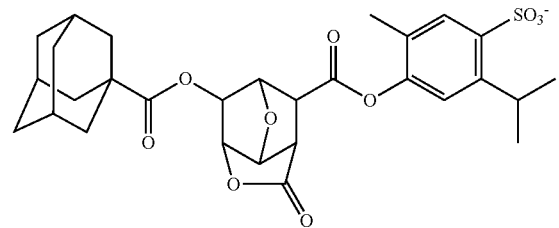
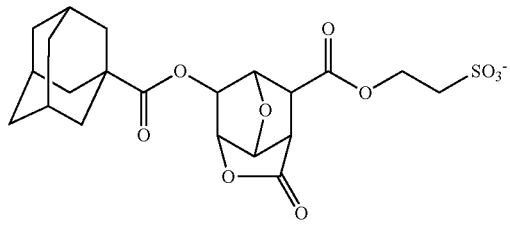
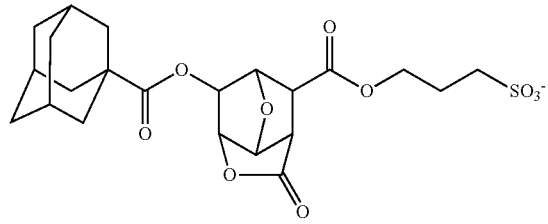
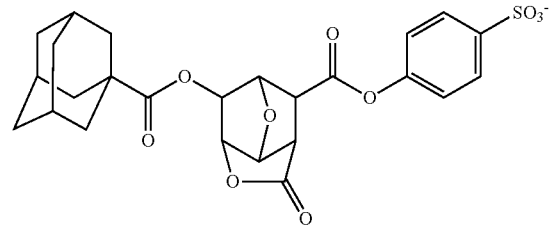
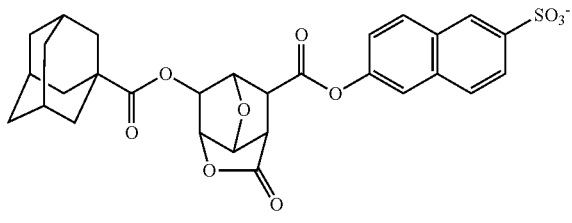
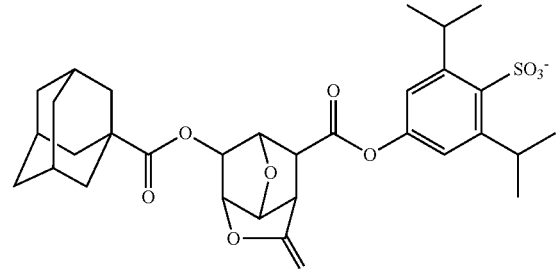
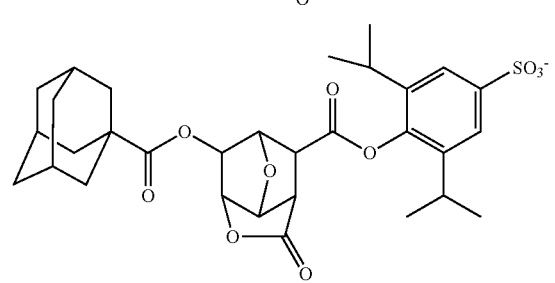
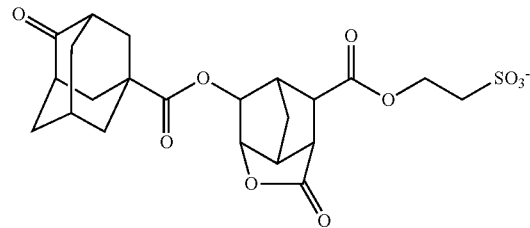
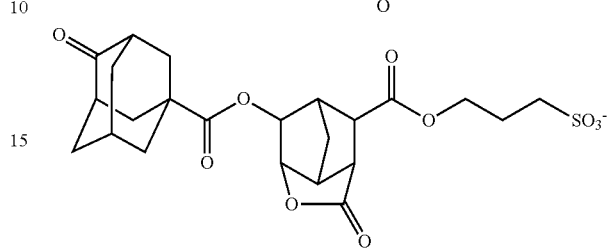
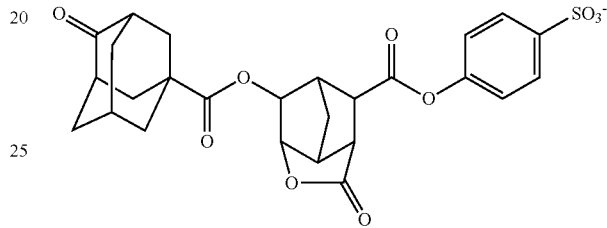
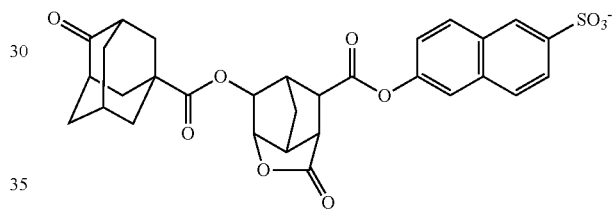
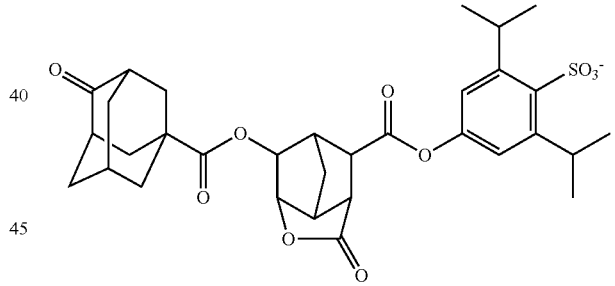
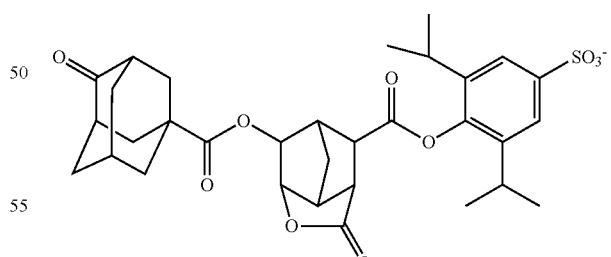
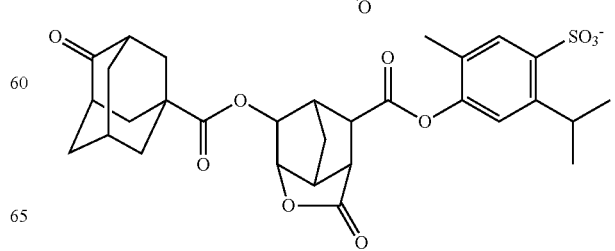

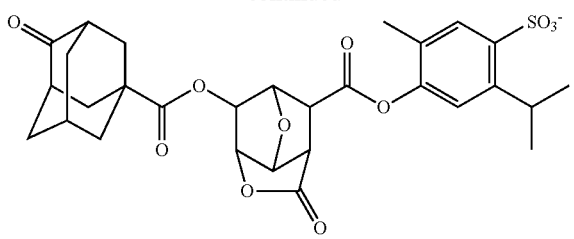
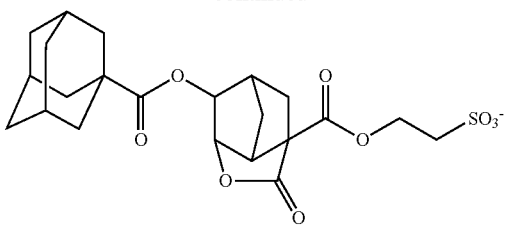
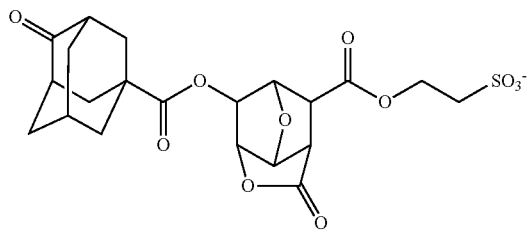
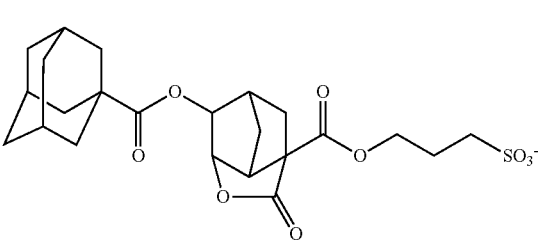
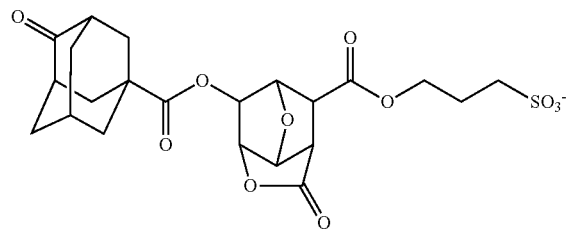
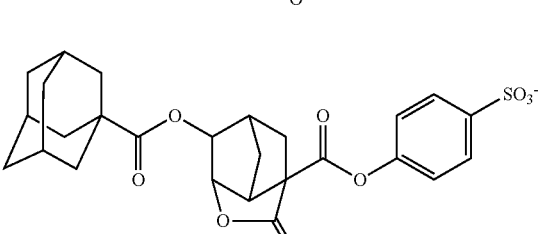
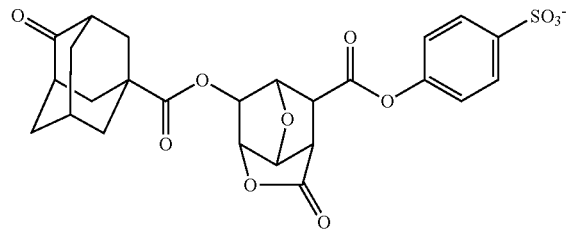
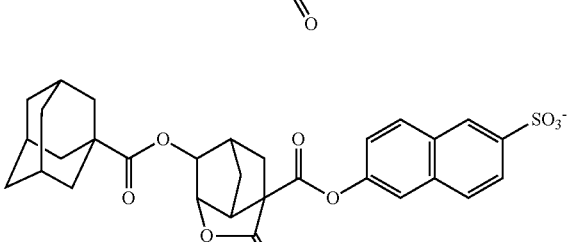
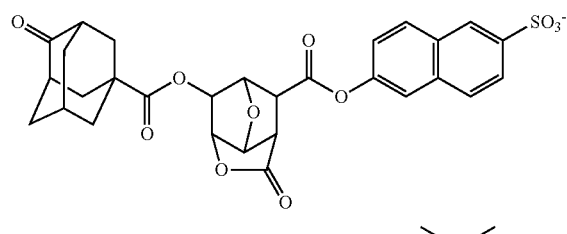
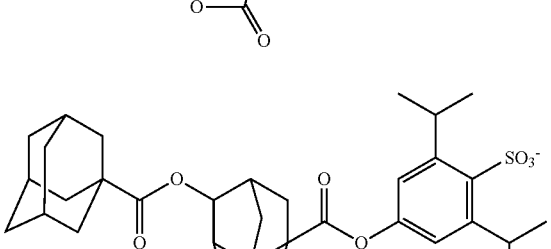
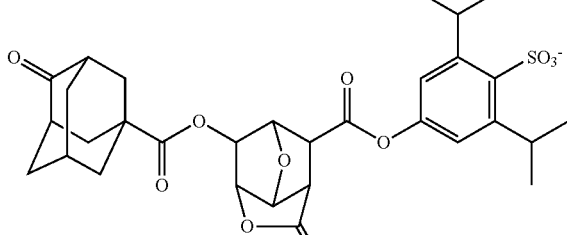
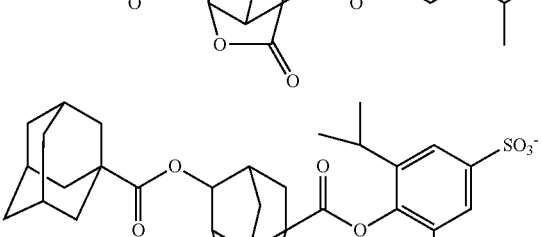
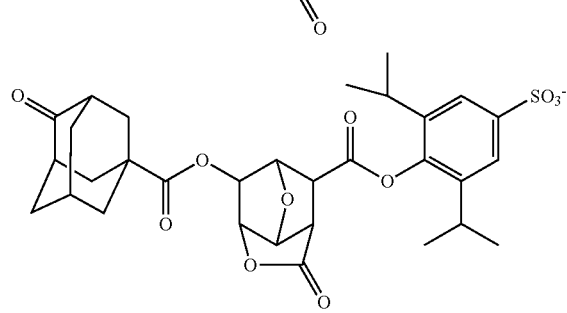
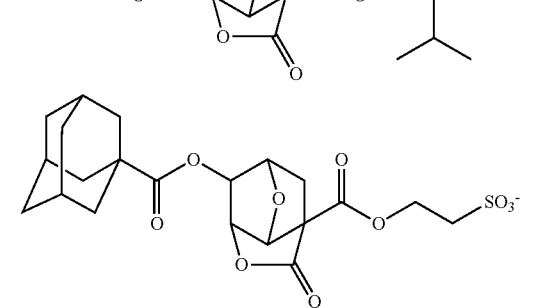

17
-continued
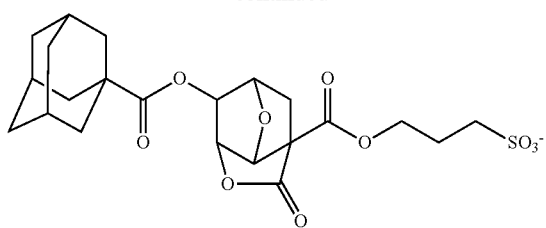
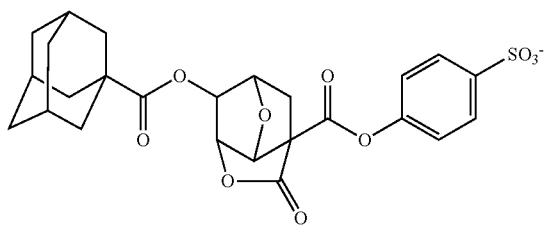
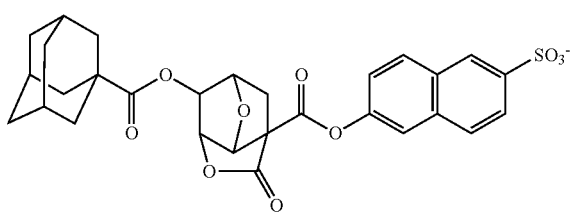
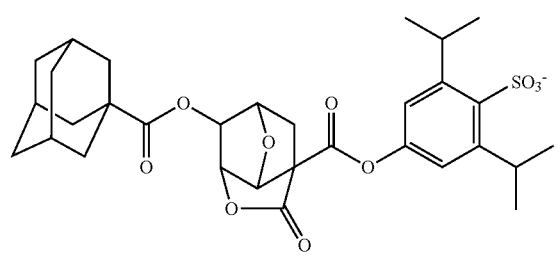
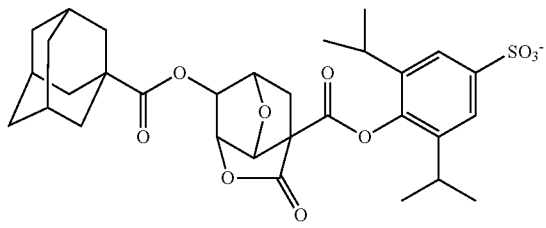
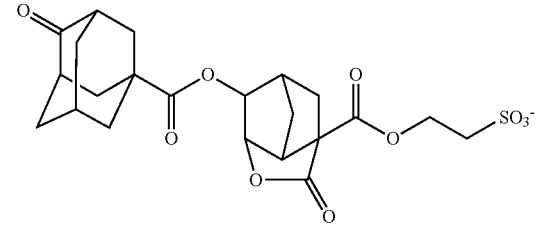
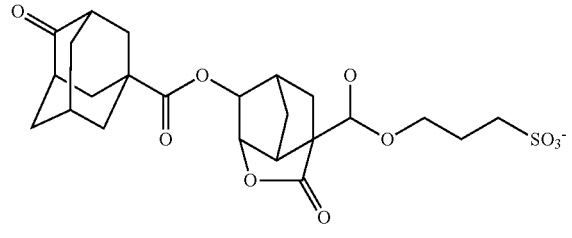
18
-continued
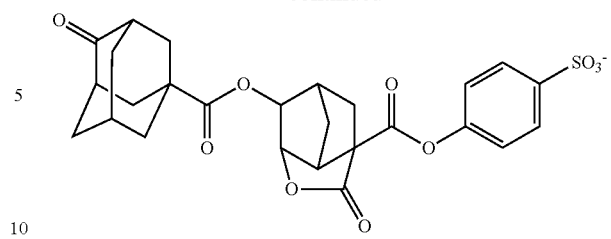
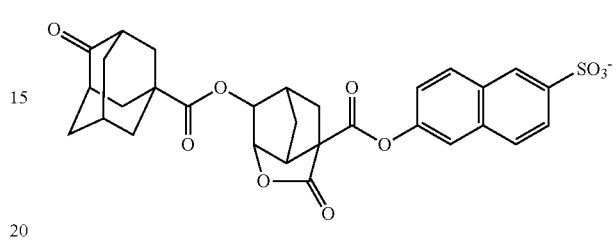
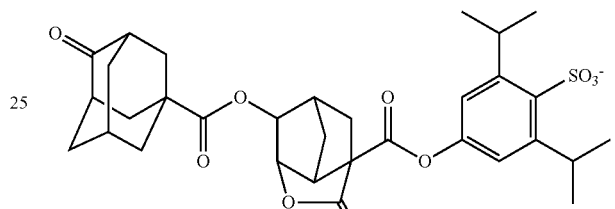
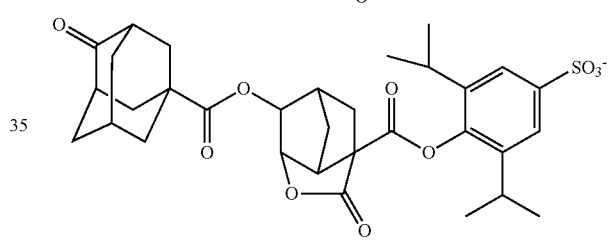
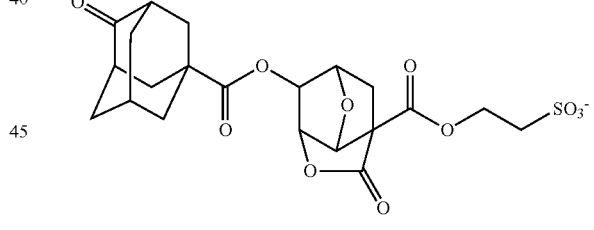
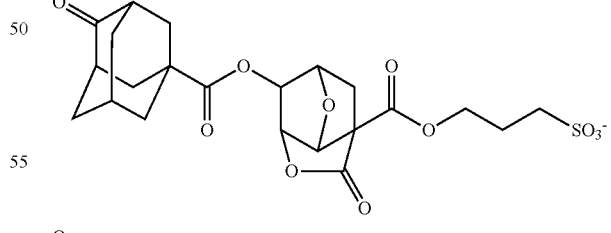
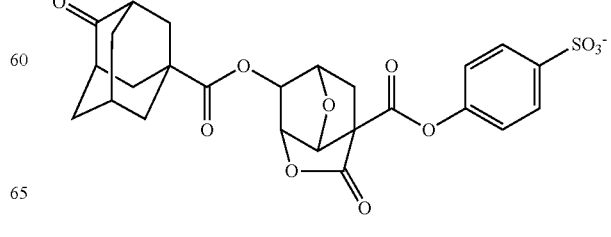

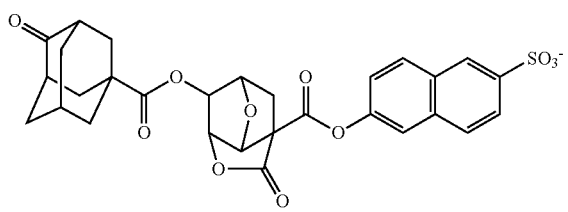

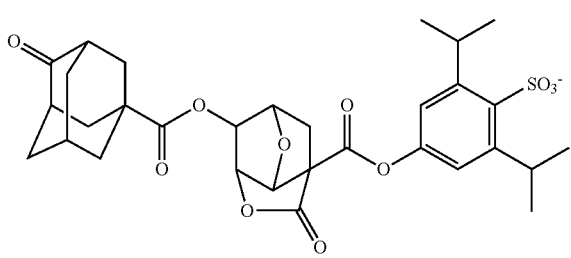

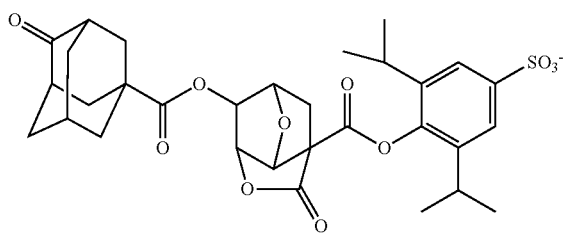

The method for preparing the sulfonium salt in monomer form having formula (1) is exemplified by the following reaction scheme, but not limited thereto.

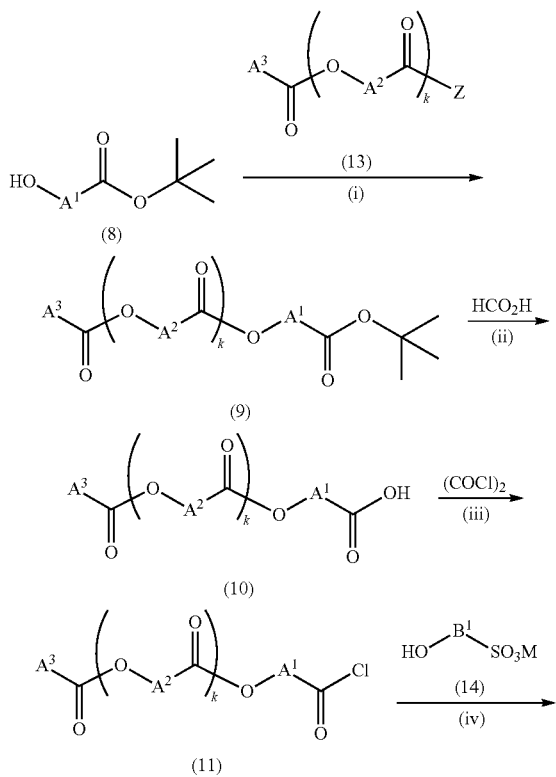

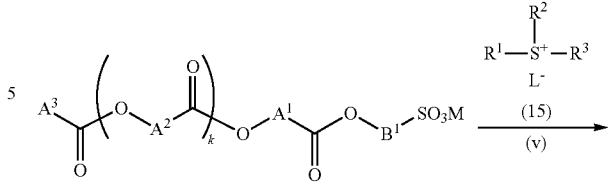

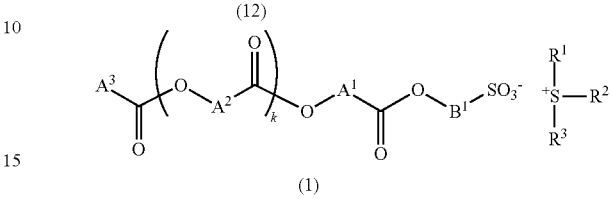

Herein $R^1$ to $R^3$, $A^1$, $A^2$, $A^3$, $B^1$ and k are as defined above. Z is a halogen atom, hydroxyl group, alkoxy group, or substituent group of the general formula (16):

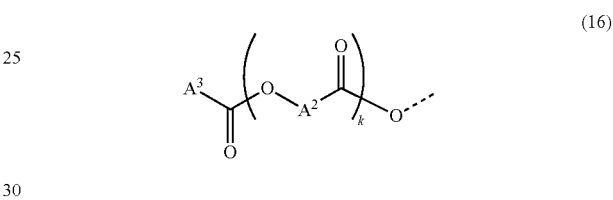

wherein $A^2$, $A^3$ and k are as defined above. $M^+$ is a lithium ion, sodium ion, potassium ion or substituted or unsubstituted ammonium ion. $L^-$ is a halide ion or methylsulfate ion.

Step (i) is reaction of hydroxy ester (8) with esterifying agent (13) to form ester (9). The reaction runs readily by any well-known procedure. The esterifying agent (13) is preferably an acid chloride of formula (13) wherein Z is chlorine, an acid anhydride of formula (13) wherein Z is a substituent group of formula (16), or a carboxylic acid of formula (13) wherein Z is hydroxyl.

Where an acid chloride or acid anhydride is used as the esterifying agent, the reaction may be conducted in a solventless system or in a solvent such as methylene chloride, toluene, hexane, diethyl ether, tetrahydrofuran, or acetonitrile, by sequentially or simultaneously adding the hydroxy ester (8), the carboxylic acid chloride or carboxylic acid anhydride corresponding to formula (13), and a base (e.g., triethylamine, pyridine or 4-dimethylaminopyridine) and allowing the reaction to take place while cooling or heating if necessary.

Where a carboxylic acid is used as the esterifying agent, the reaction may be conducted in a solvent such as toluene or hexane by heating the hydroxy ester (8) and corresponding carboxylic acid in the presence of an acid catalyst, and optionally removing the water formed during reaction from the system. Suitable acid catalysts include mineral acids such as hydrochloric acid, sulfuric acid, nitric acid and perchloric acid and organic acids such as p-toluenesulfonic acid and benzenesulfonic acid.

Step (ii) is deprotection of tert-butyl group from the ester (9) to form carboxylic acid (10). The ester (9) is dissolved in formic acid as a solvent. The solution is stirred with optional cooling or heating, until the carboxylic acid (10) is obtained.

Step (iii) is to convert the carboxylic acid (10) to acid chloride (11). The reaction may be conducted in a solvent such as methylene chloride, toluene, hexane, diethyl ether, tetrahydrofuran or acetonitrile, by sequentially or simultaneously adding the carboxylic acid (10) and a chlorinating agent such as oxalyl dichloride while optionally cooling or heating.

Step (iv) is nucleophilic displacement reaction between the acid chloride (11) and sulfo alcohol (14) to form sulfonic acid salt (12). The reaction may be readily conducted in any well-known manner by sequentially or simultaneously adding the acid chloride (11), sulfo alcohol (14), and a base to a solvent while cooling or heating if necessary.

Suitable solvents which can be used in step (iv) include water; ethers such as tetrahydrofuran, diethyl ether, diisopropyl ether, di-n-butyl ether and 1,4-dioxane; hydrocarbons such as n-hexane, n-heptane, benzene, toluene, and xylene; aprotic polar solvents such as acetonitrile, dimethyl sulfoxide (DMSO) and N,N-dimethylformamide (DMF); and chlorinated solvents such as methylene chloride, chloroform and carbon tetrachloride. The solvent may be selected depending on reaction conditions while it may be used alone or in admixture.

Suitable bases which can be used in step (iv) include amines such as ammonia, triethylamine, pyridine, lutidine, collidine, and N,N-dimethylaniline; hydroxides such as sodium hydroxide, potassium hydroxide and tetramethylammonium hydroxide; and carbonates such as potassium carbonate and sodium hydrogencarbonate, which may be used alone or in admixture.

Step (v) is ion exchange reaction between sulfonic acid salt (12) and sulfonium salt (15) to form sulfonium salt (1). As the sulfonic acid salt (12), the reaction product resulting from step (iv) may be used in crude form or after it is isolated by customary aqueous work-up.

Where the isolated form of sulfonic acid salt (12) is used, a reaction mixture is obtained by dissolving the salt in a solvent, mixing with sulfonium salt (15), and optionally cooling or heating. Examples of the solvent used herein include water; ethers such as tetrahydrofuran, diethyl ether, diisopropyl ether, di-n-butyl ether and 1,4-dioxane; hydrocarbons such as n-hexane, n-heptane, benzene, toluene, and xylene; aprotic polar solvents such as acetonitrile, dimethyl sulfoxide (DMSO) and N,N-dimethylformamide (DMF); and chlorinated solvents such as methylene chloride, chloroform and carbon tetrachloride. From the reaction mixture, sulfonium salt (1) may be recovered via customary aqueous work-up. If necessary, the salt may be purified by standard techniques like distillation, recrystallization and chromatography.

Where the crude form of sulfonic acid salt (12) is used, a reaction mixture is obtained by adding sulfonium salt (15) to the reaction mixture at the end of synthesis reaction (step iv) and optionally cooling or heating. If necessary, a solvent may be added to the reaction mixture. Examples of the solvent include water; ethers such as tetrahydrofuran, diethyl ether, diisopropyl ether, di-n-butyl ether and 1,4-dioxane; hydrocarbons such as n-hexane, n-heptane, benzene, toluene, and xylene; aprotic polar solvents such as acetonitrile, dimethyl sulfoxide (DMSO) and N,N-dimethylformamide (DMF); and chlorinated solvents such as methylene chloride, chloroform and carbon tetrachloride. From the reaction mixture, sulfonium salt (1) may be recovered via customary aqueous work-up. If necessary, the salt may be purified by standard techniques like distillation, recrystallization and chromatography.

Since the sulfonium salt of formula (1) according to the invention has a sulfonium salt structure of non-fluorinated sulfonic acid, it generates an acid with appropriate strength upon exposure to high-energy radiation. Since the sulfonium salt has a bulky substituent group, the movement and diffusion of the generated acid can be controlled, contributing to roughness improvement. Since the sulfonium salt is fully lipophilic, it is easy to prepare and handle.

Understandably, any corresponding onium salts such as iodonium and ammonium salts may be synthesized by the same method as the synthesis of the sulfonium salt having formula (1). These onium salts may be equally applicable to chemically amplified resist compositions.

Examples of the iodonium cation include diphenyliodonium, bis(4-methylphenyl)iodonium, bis(4-(1,1-dimethylethyl)phenyl)iodonium, bis(4-(1,1-dimethylpropyl)phenyl)iodonium, and (4-(1,1-dimethylethoxyl)phenyl)phenyliodonium. Examples of the ammonium cation include tertiary ammonium cations such as trimethylammonium, triethylammonium, tributylammonium, and N,N-dimethylanilinium, and quaternary ammonium cations such as tetramethylammonium, tetraethylammonium, and tetrabutylammonium. These iodonium and ammonium salts may be used as exerting a photoacid generating effect or thermal acid generating effect.

Resist Composition

Another embodiment of the invention is a resist composition comprising a sulfonium salt having formula (1) capable of generating a sulfonic acid having the following formula (1a) in response to high-energy radiation or heat, as an acid generator.

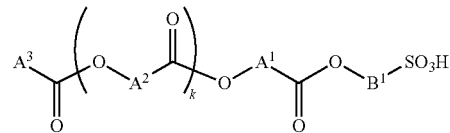

Herein $A^1$, $A^2$, $A^3$, $B^1$, and k are as defined above.

Typical of the resist composition is a chemically amplified resist composition comprising the acid generator defined herein, a base resin, and an organic solvent. In this embodiment, when the sulfonium salt is formulated as the acid generator, its amount is preferably 0.1 to 40 parts, more preferably 1 to 20 parts by weight per 100 parts by weight of the base resin. If the amount of sulfonium salt exceeds 40 pbw, the composition may have an excessively high sensitivity and lack shelf stability. If the amount of sulfonium salt is less than 0.1 pbw, an amount of acid generated may be insufficient to deprotect the acid labile group.

When a positive resist composition is prepared, a polymer adapted to be decomposed under the action of acid to increase its solubility in alkaline developer is preferably used as the base resin. Desirably the resin adapted to be decomposed under the action of acid to increase its solubility in alkaline developer is a polymer comprising recurring units having the general formula (4).

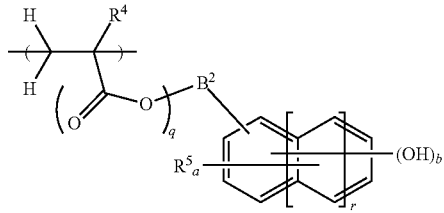

Herein q is 0 or 1, r is an integer of 0 to 2, $R^4$ is hydrogen, fluorine, methyl or trifluoromethyl, $R^5$ is each independently hydrogen or a $C_1$-$C_6$ alkyl group, $B^2$ is a single bond or a $C_1$-$C_{10}$ alkylene group which may contain an ether bond, a is an integer satisfying a≤5+2r−b, and b is an integer of 1 to 3.

Of the recurring units of formula (4), those recurring units free of the linker: —CO—O—$B^2$— are derived from monomers of hydroxyl-substituted aromatic ring having a 1-substituted or unsubstituted vinyl group bonded thereto, typically hydroxystyrene units. Preferred examples of such units are those derived from 3-hydroxystyrene, 4-hydroxystyrene, 5-hydroxy-2-vinylnaphthalene and 6-hydroxy-2-vinylnaphthalene.

Those recurring units having the linker: —CO—O—$B^2$— are derived from carbonyl-substituted vinyl monomers, typically (meth)acrylic acid esters. Examples of the recurring units having the linker: —CO—O—$B^2$—, represented by formula (4), are shown below.

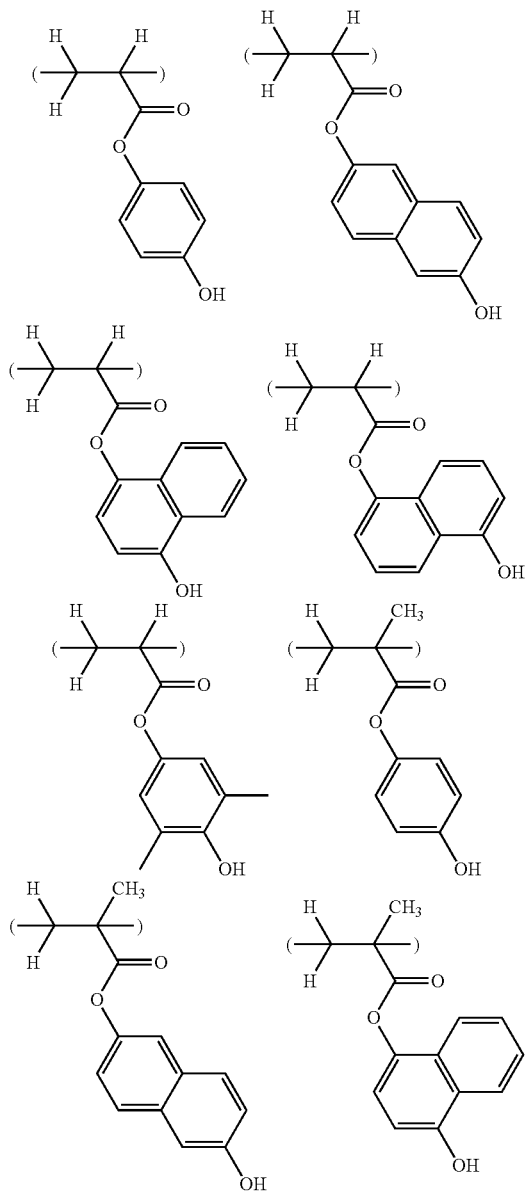

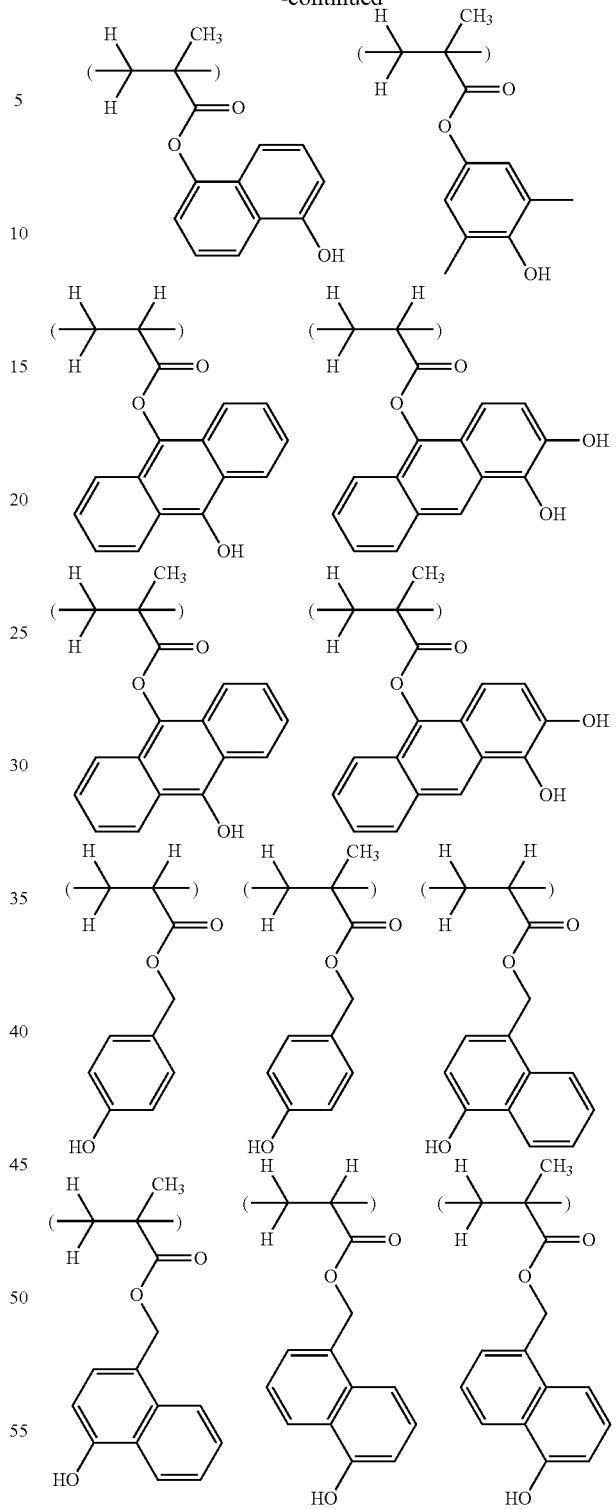

The recurring units having formula (4) may be of single type or a combination of plural types and are preferably incorporated in a range of 30 to 80 mol % based on the overall recurring units of the polymer. When units capable of affording higher etch resistance to the polymer, represented by the general formula (6) and/or (7), as described below, are incorporated in the polymer and they are substituted with a phenolic hydroxyl group, the sum of recurring units having formula (4) plus recurring units having formula (6) and/or (7) should fall in the above-defined range.

In order that the resist composition be of positive tone in that exposed regions of resist film become soluble in aqueous alkaline solution, the polymer should preferably further comprise units having an acid labile group-protected acidic functional group, that is, units which are protected with an acid labile group, but turn alkali soluble under the action of acid. The units which are protected with an acid labile group, but turn alkali soluble under the action of acid are most preferably recurring units having the general formula (5).

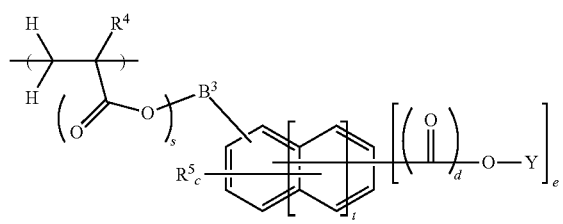

(5)

Herein s is 0 or 1, t is an integer of 0 to 2, $R^4$ and $R^5$ are as defined above, $B^3$ is a single bond or a $C_1$-$C_{10}$ alkylene group which may contain an ether bond, c is an integer satisfying c≤5+2t−e, d is 0 or 1, e is an integer of 1 to 3, Y is an acid labile group when e=1, Y is hydrogen or an acid labile group when e=2 or 3, with at least one Y being an acid labile group.

The subscript c is an integer satisfying c≤5+2t−e, specifically c=5+2t−e when all $R^5$ are hydrogen, and c is an integer of 0 to 3 when all $R^5$ are $C_1$-$C_6$ alkyl.

The unit of formula (5) corresponds to a unit of formula (4) and differs therefrom in that at least one phenolic hydroxyl group substituted on aromatic ring is protected with an acid labile group, or at least one phenolic hydroxyl group is substituted by a carboxyl group which is protected with an acid labile group. The acid labile group may be any of acid labile groups which are eliminatable with acid to give an acidic group, as used in numerous well-known chemically amplified resist compositions. Inter alia, acetal groups are preferred.

Where the phenolic hydroxyl group or carboxyl group mentioned above is protected with a tertiary alkyl group, those alkyl groups of 4 to 18 carbon atoms are preferred because the monomers for polymerization are available via distillation. The alkyl substituents on tertiary carbon of the tertiary alkyl group are typically straight, branched or cyclic alkyl groups of 1 to 15 carbon atoms which may partially contain an oxygen-containing functionality such as ether bond or carbonyl. The alkyl substituents on tertiary carbon may bond together to form a ring.

Preferred examples of the alkyl substituent include, but are not limited to, methyl, ethyl, propyl, adamantyl, norbornyl, tetrahydrofuran-2-yl, 7-oxanorbornan-2-yl, cyclopentyl, 2-tetrahydrofuryl, tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, tetracyclo[4.4.0.1$^{2,5}$.1$^{7,10}$]dodecyl, and 3-oxo-1-cyclohexyl. Examples of the tertiary alkyl group include, but are not limited to, tert-butyl, tert-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexyl-cyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

Acetal groups of the general formula (17):

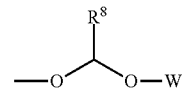

(17)

wherein $R^8$ is hydrogen or a straight, branched or cyclic $C_1$-$C_{10}$ alkyl group, and W is a straight, branched or cyclic $C_1$-$C_{30}$ alkyl group are often used as the acid labile group. These acetal groups offer a choice of acid labile groups that ensure formation of patterns which are rectangular at the interface between the pattern and the substrate. Acetal groups containing a polycyclic alkyl group of 7 to 30 carbon atoms are preferred for higher resolution. Where W contains a polycyclic alkyl group, preferably a bond forms between the secondary carbon of the polycyclic structure and the acetal oxygen. This is because the polymer becomes unstable if the bond is on the tertiary carbon of the cyclic structure, suggesting that the resist composition lacks shelf stability and resolution. Inversely, when W bonds to the acetal oxygen on the primary carbon via straight alkyl of at least one carbon, the polymer may have a low glass transition temperature (Tg), suggesting that the resist pattern after development is degraded in profile by bake.

Examples of the acetal group of formula (17) are shown below.

Herein $R^8$ is as defined above.

While $R^8$ is hydrogen or a straight, branched or cyclic $C_1$-$C_{10}$ alkyl group, it is properly selected depending on the design of sensitivity of labile group to acid. For example, if the labile group is designed so as to be decomposed with strong acid while ensuring relatively high stability, then hydrogen is selected. If the labile group is designed to be highly reactive to exhibit high sensitivity to pH changes, a straight alkyl group is selected. If the labile group is substituted at the end with a relatively higher alkyl group and designed to exhibit a large solubility change by decomposition, $R^8$ is preferably an alkyl group whose carbon having a bond to acetal carbon is secondary carbon, although the choice of $R^8$ depends on a combination with the acid generator and basic compound formulated in the resist composition. Examples of group $R^8$ bonding to acetal carbon via secondary carbon include isopropyl, sec-butyl, cyclopentyl, and cyclohexyl.

Another choice of acid labile group is by bonding (—$CH_2COO$-tertiary alkyl group) to a phenolic hydroxyl group. The tertiary alkyl group used herein may be the same as the aforementioned tertiary alkyl group used for the protection of phenolic hydroxyl groups.

The units which are protected with an acid labile group, but turn alkali soluble under the action of acid, represented by formula (5), may be used alone or in admixture of two or more. The units of formula (5) are preferably incorporated in a range of 5 to 45 mol % based on the overall recurring units of the polymer.

In a preferred embodiment, the polymer may further comprise recurring units having the general formula (6) and/or (7) as main constituent units.

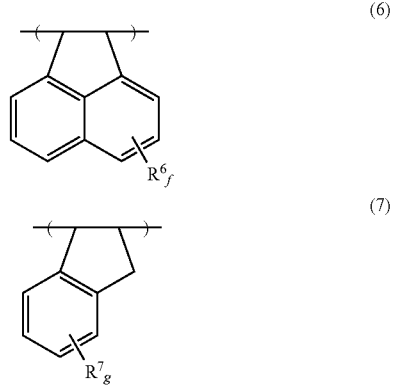

Herein f is an integer of 0 to 6, $R^6$ is each independently hydrogen, an optionally halo-substituted $C_1$-$C_6$ alkyl or primary or secondary alkoxy group, or an optionally halo-substituted $C_1$-$C_7$ alkylcarbonyloxy group, g is an integer of 0 to 4, and $R^7$ is each independently hydrogen, an optionally halo-substituted $C_1$-$C_6$ alkyl or primary or secondary alkoxy group, or an optionally halo-substituted $C_1$-$C_7$ alkylcarbonyloxy group.

When the recurring units of at least one type selected from recurring units having formulae (6) and (7) are incorporated, etching resistance is further improved because not only the aromatic ring possesses etching resistance, but the cyclic structure incorporated into the main chain also exerts the effect of improving resistance to EB irradiation during etching and pattern inspection steps.

The recurring units having formulae (6) and (7) which incorporate a cyclic structure into the main chain to improve etching resistance may be of one type or a combination of plural types. The units of formulae (6) and (7) are preferably incorporated in a range of at least 5 mol % based on the overall recurring units of the polymer in order to exert an effect of improving etching resistance. Where the units of formulae (6) and (7) have a functional group with polarity so that the units are capable of providing adhesion to the substrate, or where the units of formulae (6) and (7) have a substituent group protected with the aforementioned acid labile group so that the units turn alkali soluble under the action of acid, the amount of these units incorporated is included in the range defined above for the corresponding units. Where the units of formulae (6) and (7) are free of functional groups or the units of formulae (6) and (7) have a functional group which is outside the above concept, the amount of these units is preferably up to 30 mol % because the occurrence of development defects is eliminated.

The units of formulae (4) and (5) and optional units of formulae (6) and (7) should preferably account for at least 60 mol % of overall monomeric units of the polymer because the range ensures that the polymer provides the resist composition with desired properties. Their amount is more preferably at least 70 mol %, and most preferably at least 85 mol %.

Where all constituent units are units selected from formulae (4) to (7), the polymer has both high etching resistance and high resolution. Recurring units other than formulae (4) to (7), which can be incorporated in the polymer, include (meth) acrylate units protected with a customary acid labile group and (meth)acrylate units having an adhesive group typically lactone structure. Although the properties of a resist film may be finely adjusted by incorporating such other recurring units, the other recurring units are not essential.

The polymer may be prepared by any well-known methods, for example, by selecting suitable monomers, and copolymerizing them while protection and deprotection reactions may be combined if necessary. The copolymerization reaction is preferably radical or anion polymerization, but not limited thereto. For the polymerization reaction, reference should be made to, for example, WO 2006/121096, JP-A 2008-102383, JP-A 2008-304590, and JP-A 2004-115630.

The polymer serving as the base resin in the resist composition should preferably have a weight average molecular weight (Mw) in the range of 2,000 to 50,000, and more preferably 3,000 to 20,000, as measured by gel permeation chromatography (GPC) versus polystyrene standards using tetrahydrofuran solvent. As long as Mw is at least 2,000, a phenomenon that pattern top is rounded to invite a drop of resolution and degradation of LER as is known in the art is eliminated. If Mw increases beyond the necessity, there is a tendency to increase LER, though depending on a particular pattern to be resolved. It is thus recommended to control the Mw to 50,000 or lower, with a Mw of 20,000 or lower being preferred particularly when it is desired to form a pattern with a line width of up to 100 nm.

The polymer should preferably have a narrow dispersity (Mw/Mn) of 1.0 to 2.0, especially 1.0 to 1.8. The narrow dispersity eliminates a possibility that foreign matter is left on the pattern or the pattern profile is degraded after development.

The polymer is advantageously used as a base resin in the resist composition along with the inventive sulfonium salt. The resist composition may exert fundamental resist performance when a solvent is added thereto. If necessary, a basic compound, acid generator (other than the inventive sulfonium salt), another polymer, surfactant, and the like may be added.

In fact, the basic compound is an essential component in chemically amplified resist compositions. The basic compound is preferably added to the resist composition of the invention as well in order to provide a high resolution or to adjust to a proper sensitivity. An appropriate amount of the basic compound added is 0.01 to 5 parts, more preferably 0.05 to 3 parts by weight per 100 parts by weight of the polymer. A choice may be made of numerous basic compounds which are known in the art as disclosed in Patent Documents 1 and 2, JP-A 2000-159758, JP-A 2007-182488, and WO 2006/121096. Known basic compounds include primary, secondary and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amides, imides, carbamates, and ammonium salts. Many examples of these compounds are described in Patent Document 2, and any of them may be used herein. Two or more basic compounds may be selected and used in admixture. Preferred examples of the basic compound to be formulated include tris(2-(methoxymethoxy)ethyl)amine, tris(2-(methoxymethoxy)ethyl)amine-N-oxide, morpholine derivatives, and imidazole derivatives.

An amine is effective when a resist pattern is formed on a substrate, typically a substrate having a surface layer of chromium compound, which is susceptible to a phenomenon that the resist film becomes substantially insoluble at the substrate interface during pattern formation, known as a footing phenomenon. Specifically, an amine compound or amine oxide compound having a carboxyl group, but free of hydrogen in covalent bond with nitrogen serving as basic center (exclusive of those amine and amine oxide compounds whose nitrogen atom is contained in the cyclic structure of aromatic ring) is effectively used for improving the pattern profile.

Preferred examples of the amine or amine oxide compound having a carboxyl group, but free of hydrogen in covalent bond with nitrogen serving as basic center include compounds of the general formulae (18) to (20), but are not limited thereto.

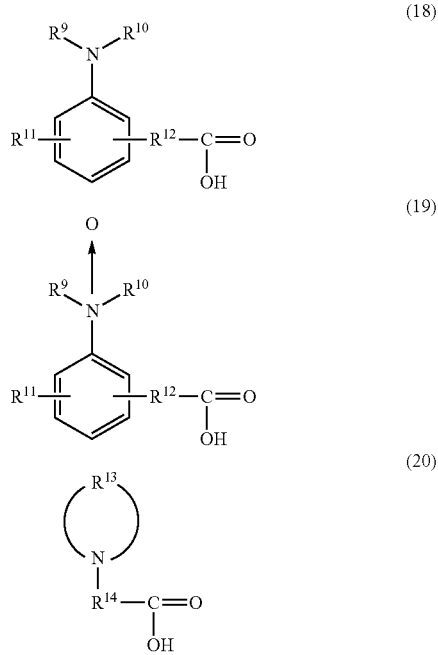

Herein $R^9$ and $R^{10}$ are each independently a straight, branched or cyclic $C_1$-$C_{20}$ alkyl group, $C_6$-$C_{20}$ aryl group, $C_7$-$C_{20}$ aralkyl group, $C_2$-$C_{10}$ hydroxyalkyl group, $C_2$-$C_{10}$ alkoxyalkyl group, $C_2$-$C_{10}$ acyloxyalkyl group, or $C_1$-$C_{10}$ alkylthioalkyl group. $R^9$ and $R^{10}$ may bond together to form a ring with the nitrogen atom to which they are attached. $R^{11}$ is hydrogen, a straight, branched or cyclic $C_1$-$C_{20}$ alkyl group, $C_6$-$C_{20}$ aryl group, $C_7$-$C_{20}$ aralkyl group, $C_1$-$C_{10}$ hydroxyalkyl group, $C_2$-$C_{10}$ alkoxyalkyl group, $C_2$-$C_{11}$ acyloxyalkyl group, $C_1$-$C_{11}$ alkylthioalkyl group, or halogen. $R^{12}$ is a single bond, a straight, branched or cyclic $C_1$-$C_{20}$ alkylene group, or $C_6$-$C_{20}$ arylene group. $R^{13}$ is an optionally substituted, straight or branched $C_2$-$C_{20}$ alkylene group whose carbon-carbon linkage may be separated by at least one carbonyl (—CO—), ether (—O—), ester (—COO—) or sulfide (—S—) group. $R^{14}$ is a straight, branched or cyclic $C_1$-$C_{20}$ alkylene group or $C_6$-$C_{20}$ arylene group.

Exemplary groups in these structural formulae are given below, but not limited thereto. Suitable $C_6$-$C_{20}$ aryl groups include phenyl, naphthyl, anthryl, phenanthryl, pyrenyl, naphthacenyl, and fluorenyl. Suitable straight, branched or cyclic $C_1$-$C_{20}$ alkyl groups include methyl, ethyl, propyl, isopropyl, butyl, isobutyl, t-butyl, pentyl, hexyl, decyl, cyclopentyl, cyclohexyl, and decahydronaphthalenyl. Suitable $C_7$-$C_{20}$ aralkyl groups include benzyl, phenethyl, phenylpropyl, naphthylmethyl, naphthylethyl, and anthracenylmethyl.

Suitable $C_1$-$C_{10}$ hydroxyalkyl groups include hydroxymethyl, hydroxyethyl, and hydroxypropyl. Suitable $C_2$-$C_{10}$ alkoxyalkyl groups include methoxymethyl, 2-methoxyethyl, ethoxymethyl, 2-ethoxyethyl, propoxymethyl, 2-propoxyethyl, butoxymethyl, 2-butoxyethyl, amyloxymethyl, 2-amyloxyethyl, cyclohexyloxymethyl, 2-cyclohexyloxyethyl, cyclopentyloxymethyl, 2-cyclopentyloxyethyl, and isomers of their alkyl moiety. Suitable $C_2$-$C_{11}$ acyloxyalkyl groups include formyloxymethyl, acetoxymethyl, propionyloxymethyl, butyryloxymethyl, pivaloyloxymethyl, cyclohexanecarbonyloxymethyl, and decanoyloxymethyl. Suitable $C_1$-$C_{11}$ alkylthioalkyl groups include methylthiomethyl, ethylthiomethyl, propylthiomethyl, isopropylthiomethyl, butylthiomethyl, isobutylthiomethyl, t-butylthiomethyl, t-amylthiomethyl, decylthiomethyl, and cyclohexylthiomethyl.

Preferred examples of the amine compound of formula (18) include, but are not limited thereto, o-dimethylaminobenzoic acid, p-dimethylaminobenzoic acid, m-dimethylaminobenzoic acid, p-diethylaminobenzoic acid, p-dipropylaminobenzoic acid, p-dibutylaminobenzoic acid, p-dipentylaminobenzoic acid, p-dihexylaminobenzoic acid, p-diethanolaminobenzoic acid, p-diisopropanolaminobenzoic acid, p-dimethanolaminobenzoic acid, 2-methyl-4-diethylaminobenzoic acid, 2-methoxy-4-diethylaminobenzoic acid, 3-dimethylamino-2-naphthalenic acid, 3-diethylamino-2-naphthalenic acid, 2-dimethylamino-5-bromobenzoic acid, 2-dimethylamino-5-chlorobenzoic acid, 2-dimethylamino-5-iodobenzoic acid, 2-dimethylamino-5-hydroxybenzoic acid, 4-dimethylaminophenylacetic acid, 4-dimethylaminophenylpropionic acid, 4-dimethylaminophenylbutyric acid, 4-dimethylaminophenylmalic acid, 4-dimethylaminophenylpyruvic acid, 4-dimethylaminophenyllactic acid, 2-(4-dimethylaminophenyl)benzoic acid, and 2-(4-(dibutylamino)-2-hydroxybenzoyl)benzoic acid.

Preferred examples of the amine oxide compound of formula (19) include oxidized forms of exemplary amine compounds of formula (18), but are not limited thereto.

Preferred examples of the amine compound of formula (20) include, but are not limited thereto, 1-piperidinepropionic acid, 1-piperidinebutyric acid, 1-piperidinemalic acid, 1-piperidinepyruvic acid, and 1-piperidinelactic acid.

The amine oxide compounds having formula (19) may be readily synthesized by the method of JP-A 2008-102383, and suitable examples of the amine oxide compound are described therein.

In the resist composition, the polymer comprising units selected from formulae (4) to (7) may be used alone or in admixture of two or more as the base resin. The base resin may include another polymer having a dissolution rate in alkaline developer that increases under the action of acid, or another polymer which is alkali soluble independent of reaction with acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymerization (ROMP) polymers, (iv) vinyl ether-maleic anhydride-(meth)acrylic acid derivative copolymers, and (v) polyhydroxystyrene derivatives. These belong to polymers adapted to turn alkali soluble under the action of acid, which are well known for use in chemically amplified positive resist compositions. Also, an alkali soluble polymer may be added for the purposes of improving pattern profile and controlling the occurrence of residues after development. Such a polymer may be selected from numerous polymers which are well known for use in chemically amplified negative resist compositions. Furthermore, a fluorinated polymer may also be added as disclosed in JP-A 2008-304590.

When the inventive polymer comprising units selected from formulae (4) to (7) and the other polymer are used in blend, the inventive polymer should preferably account for at least 30%, more preferably at least 50% by weight of the polymer blend. Use of at least 30% by weight of the inventive polymer is preferred because the formation of defects during development is prevented. However, it is also preferred to blend the inventive polymer in such an amount that the proportion of aromatic ring-bearing units may not fall below 60 mol % based on overall recurring units of polymers in the blend. The other polymer is not limited to one type and a mixture of two or more polymers may be added. The use of plural polymers allows for adjustment of resist properties.

Optionally, the resist composition of the invention may further comprise a surfactant which is commonly used for facilitating the coating operation. It may be selected from numerous well-known surfactants as described in WO 2006/121096, JP-A 2008-102383, JP-A 2008-304590, JP-A 2004-115630, and JP-A 2005-008766 and in accordance with the teaching thereof. The surfactant may be added in an amount of preferably up to 2 parts, more preferably 0.01 to 1 part by weight per 100 parts by weight of the base resin.

Patterning Process

For pattern formation from the resist composition, any well-known lithography processes may be used. In general, the resist composition is applied onto a substrate on which an integrated circuit is to be formed (e.g., Si, SiO$_2$, SiN, SiON, TiN, WSi, BPSG, SOG or organic antireflective coating) or a substrate on which a mask circuit is to be formed (e.g., Cr, CrO, CrON or MoSi) by a suitable coating technique, typically spin coating. The coating is prebaked on a hot plate at a temperature of 60 to 150° C. for 1 to 20 minutes, preferably 80 to 140° C. for 1 to 10 minutes. The resulting resist film is typically 0.05 to 2.0 μm thick.

With a mask having a desired pattern placed above the resist film, the resist film is then exposed to high-energy radiation such as deep-UV, excimer laser light, x-ray or EB in an exposure dose preferably in the range of 1 to 200 mJ/cm$^2$, more preferably 10 to 100 mJ/cm$^2$. Alternatively, a pattern may be directly written with a beam, typically EB, without a need for mask. The chemically amplified resist composition of the invention is advantageous particularly on patternwise exposure to EUV or EB. Light exposure may be done by a conventional lithography process or in some cases, by an immersion lithography process of providing liquid immersion, typically water, between the mask and the resist film. In the case of immersion lithography, a protective film which is insoluble in water may be used.

The resist film is further baked on a hot plate at 60 to 150° C. for 1 to 20 minutes, preferably 80 to 140° C. for 1 to 5 minutes (post-exposure baking=PEB). Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray techniques. In this way, a desired resist pattern is formed on the substrate.

The resist composition of the invention is advantageous particularly on use under the situation that requires high etching resistance, and a minimal change of pattern line width and minimal LER even when the time duration from exposure to PEB is prolonged. It is also advantageous for pattern formation on a processable substrate, typically a substrate having a surface layer of material to which the resist pattern is less adherent with a likelihood of pattern stripping or pattern collapse, specifically a substrate having sputter deposited thereon a layer of metallic chromium or a chromium compound containing one or more light elements such as oxygen, nitrogen and carbon, more specifically a photomask blank.

EXAMPLE

Examples and Comparative Examples are given below by way of illustration and not by way of limitation. All parts are by weight (pbw); Me stands for methyl; Mw is a weight average molecular weight as measured by GPC versus polystyrene standards. The copolymer compositional ratio is a molar ratio.

Synthesis Example 1

Synthesis of Sulfonium Salt

Sulfonium salts PAG-1 to PAG-4 within the scope of the invention were synthesized according to the scheme shown below. The structure of the inventive sulfonium salts PAG-1 to PAG-4 is shown in Table 5 together with the structure of comparative sulfonium salts c-PAG-1 to c-PAG-3.

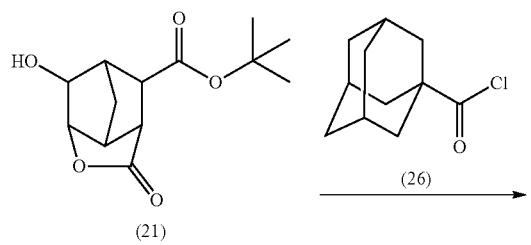

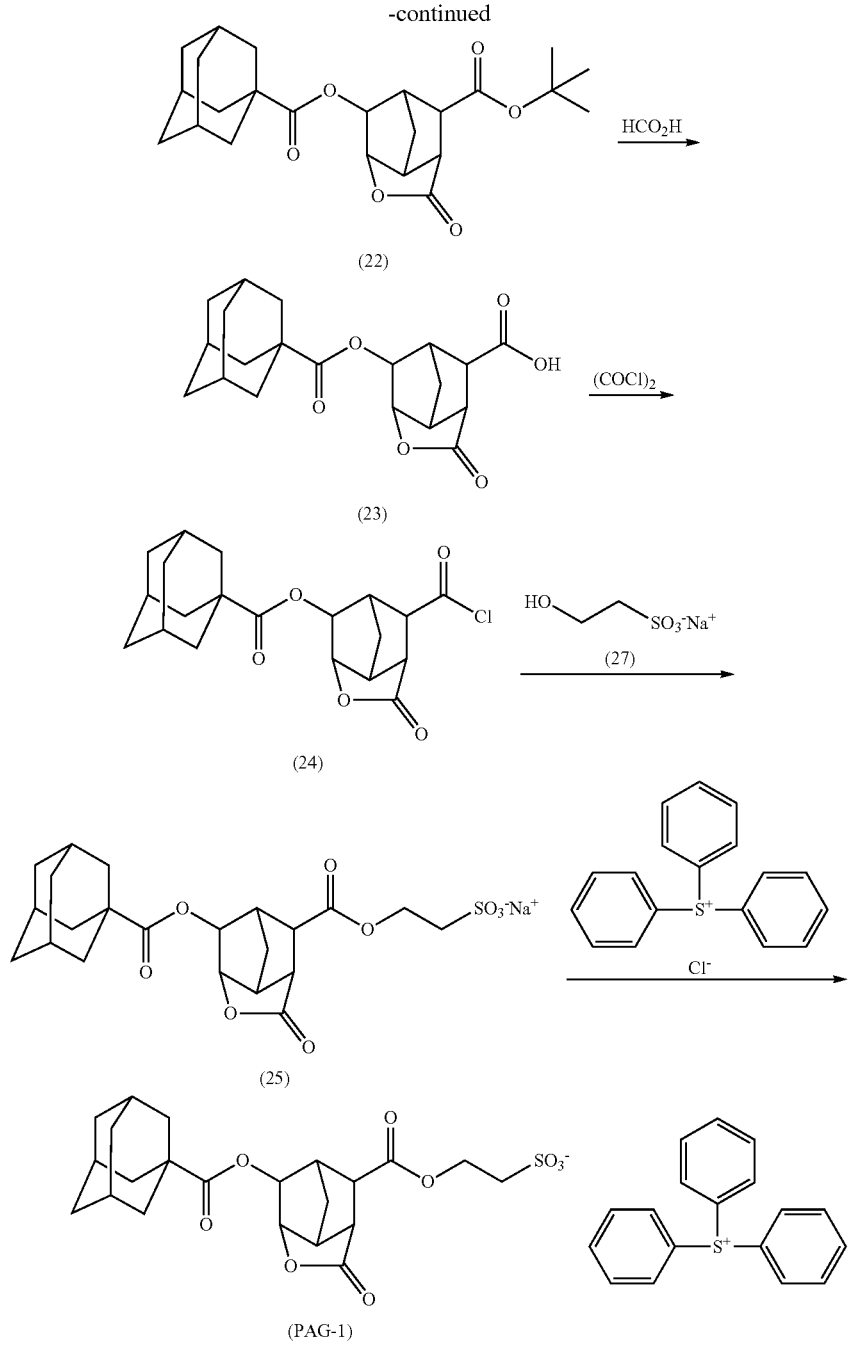

Synthesis Example 1

Synthesis of PAG-1

Synthesis Example 1-1-1

Synthesis of 7-tert-butoxycarbonyl-2-oxohexahydro-3,5-methano-2H-cyclopenta[b]furan-6-yl adamantanecarboxylate (22)

In 2,000 ml of acetonitrile were dissolved 282 g of tert-butyl 6-hydroxy-2-oxohexahydro-3,5-methano-2H-cyclopenta[b]furan-7-carboxylate (21), 157 g of triethylamine and 13.6 g of 4-dimethylaminopyridine. Below 20° C., 328 g of adamantanecarboxylic chloride (26) was added dropwise to the solution, which was stirred at room temperature for 3 hours. Then 1,000 g of water was added to the solution, followed by standard work-up. Recrystallization from methylene chloride gave 391 g of the target compound (yield 85%).

Synthesis Example 1-1-2

Synthesis of 6-adamantanecarbonyloxy-2-oxo-hexahydro-3,5-methano-2H-cyclopenta[b]furan-7-carboxylic acid (23)

The ester (22) obtained in Synthesis Example 1-1-1, 388 g, was dissolved in 1,900 g of formic acid, followed by stirring at 40° C. for 10 hours. The formic acid was distilled off in vacuum and the residue was recrystallized from ethyl acetate, obtaining 319 g of the target compound (yield 95%).

Synthesis Example 1-1-3

Synthesis of 7-chlorocarbonyl-2-oxohexahydro-3,5-methano-2H-cyclopenta[b]furan-6-yl adamantanecarboxylate (24)

In 420 ml of toluene was suspended 60 g of the carboxylic acid (23) obtained in Synthesis Example 1-1-2. At 80° C., 25.3 g of oxalyl dichloride was added dropwise to the suspension, which was stirred for 4 hours. The toluene was distilled off in vacuum, obtaining the target compound. The resulting acid chloride was used in the subsequent reaction without further purification.

Synthesis Example 1-1-4

Synthesis of triphenylsulfonium 2'-(6-adamantanecarbonyloxy-2-oxohexahydro-3,5-methano-2H-cyclopenta[b]furan-7-carbonyloxy)ethanesulfonate (PAG-1)

In 20 g of $CH_3CN$, 4.7 g of sodium 2-hydroxyethanesulfonate (27), 2.9 g of triethylamine, and 24 mg of 4-dimethylaminopyridine were dissolved. To this solution, a solution of 7.3 g of the acid chloride (24) obtained in Synthesis Example 1-1-3 in 20 g of $CH_3CN$ was added dropwise below 20° C. The combined solution was stirred at 25° C. for 2 hours, obtaining sulfonic acid salt (25). To the reaction mixture, 20 g of $CH_2Cl_2$ and 34 g of an aqueous solution of triphenylsulfonium chloride were added, followed by stirring for 30 minutes. The organic layer was separated, the aqueous layer was extracted with $CH_2Cl_2$, and the organic layers were combined and washed 3 times with $H_2O$. The solvent was distilled off in vacuum, obtaining 8.4 g of the target compound PAG-1 (three-stage yield 57%).

Synthesis Example 1-2

Synthesis of PAG-2

Synthesis was carried out by the same procedure as in Synthesis Example 1-1 aside from using 4-tert-butylphenyldiphenylsulfonium chloride instead of the aqueous solution of triphenylsulfonium chloride in Synthesis Example 1-1-4. There was obtained 13.8 g of 4-tert-butylphenyldiphenylsulfonium 2'-(6-adamantanecarbonyloxy-2-oxo-4-oxahexahydro-3,5-methano-2H-cyclopenta[b]furan-7-carbonyloxy)ethanesulfonate, designated PAG-2. Five-stage yield 60%.

Synthesis Example 1-3

Synthesis of PAG-3

In 300 g of tetrahydrofuran (THF) and 200 g of $H_2O$, were dissolved 48.8 g of sodium 4-phenolsulfonate and 40.0 g of a 25% sodium hydroxide aqueous solution. To this solution at 25° C., a THF solution of 60.0 g of the acid chloride (24) obtained in Synthesis Example 1-1-3 was added dropwise, followed by stirring at 25° C. for 2 hours. A solid precipitate was collected by filtration. To the solid, 200 g of $CH_2Cl_2$ and 67 g of an aqueous solution of triphenylsulfonium chloride were added, followed by stirring for 30 minutes. The organic layer was separated, the aqueous layer was extracted with $CH_2Cl_2$, and the organic layers were combined and washed 3 times with $H_2O$. The solvent was distilled off in vacuum, obtaining 48 g of the target compound PAG-3 (three-stage yield 74%).

Synthesis Example 1-4

Synthesis of PAG-4

Synthesis was carried out by the same procedure as in Synthesis Example 1-2 aside from using 4-tert-butylphenyldiphenylsulfonium chloride instead of the aqueous solution of triphenylsulfonium chloride in Synthesis Example 1-2. There was obtained 53.4 g of 4-tert-butylphenyldiphenylsulfonium 4-(6-adamantanecarbonyloxy-2-oxo-4-oxahexahydro-3,5-methano-2H-cyclopenta[b]furan-7-carbonyloxy)benzenesulfonate, designated PAG-4. Five-stage yield 70%.

Synthesis Example 2

Synthesis of Polymers

Polymers for use in resist compositions were synthesized according to the following formulation. The compositional proportion (in molar ratio) of polymers is shown in Table 1. The structure of recurring units is shown in Tables 2 to 4.

Synthesis Example 2-1

Synthesis of Polymer 1

A 3-L flask was charged with 407.5 g of acetoxystyrene, 42.5 g of acenaphthylene, and 1,275 g of toluene as solvent. The reactor was cooled at −70° C. in a nitrogen atmosphere, after which vacuum pumping and nitrogen blow were repeated three times. The reactor was warmed up to room temperature, whereupon 34.7 g of 2,2'-azobis(2,4-dimethylvaleronitrile) (V-65 by Wako Pure Chemical Industries, Ltd.) was added. The reactor was heated at 55° C., whereupon reaction ran for 40 hours. With stirring, a mixture of 970 g of methanol and 180 g of water was added dropwise to the reaction solution. After 30 minutes of standing, the lower layer (polymer layer) was concentrated under reduced pressure. The polymer layer concentrate was dissolved again in 0.45 L of methanol and 0.54 L of THF, to which 160 g of triethylamine and 30 g of water were added. The reaction mixture was heated at 60° C. for 40 hours for deprotection reaction. The reaction solution was concentrated under reduced pressure. To the concentrate, 548 g of methanol and 112 g of acetone were added for dissolution. With stirring, 990 g of hexane was added dropwise to the solution. After 30 minutes of standing, 300 g of THF was added to the lower layer (polymer layer). With stirring, 1,030 g of hexane was added dropwise thereto. After 30 minutes of standing, the lower layer (polymer layer) was concentrated under reduced pressure. The polymer solution was neutralized with 82 g of acetic acid. The reaction solution was concentrated, dissolved in 0.3 L of acetone, and poured into 10 L of water for precipitation. The precipitate was filtered and dried, yielding 280 g of a white polymer. The polymer was analyzed by $^1$H-NMR and GPC, with the results shown below.
Copolymer Compositional Ratio
hydroxystyrene:acenaphthylene=89.3:10.7
Mw=5,000
Mw/Mn=1.63
Under acidic conditions, 100 g of the polymer was reacted with 50 g of 2-methyl-1-propenyl methyl ether. This was followed by neutralization, phase separation, and crystallization, obtaining 125 g of a polymer, designated Polymer 1.

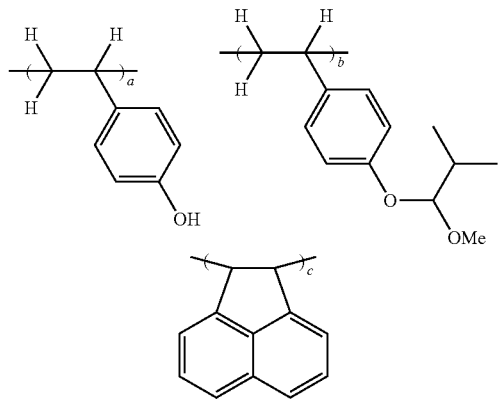

Polymer 1
(a:b:c = 70:20:10)

Synthesis Example 2-2

Synthesis of Polymer 2

Polymer 2 was synthesized by the same procedure as in Synthesis Example 2-1 aside from using 2-methyl-1-propenyl 8-tricyclo[5.2.1.0$^{2,6}$]decanyl ether instead of 2-methyl-1-propenyl methyl ether.

Synthesis Example 2-3

Synthesis of Polymer 3

Polymer 3 was synthesized by the same procedure as in Synthesis Example 2-1 aside from using 2-methyl-1-propenyl 2-adamantyl ether instead of 2-methyl-1-propenyl methyl ether.

Synthesis Example 2-4

Synthesis of Polymer 4

In nitrogen atmosphere, 362 g of 4-hydroxyphenyl methacrylate, 38.2 g of acenaphthylene, 40.9 g of dimethyl 2,2'-azobis(2-methylpropionate) (V-601 by Wako Pure Chemical Industries, Ltd.), and 500 g of methyl ethyl ketone were fed into a dropping cylinder to form a monomer solution. A flask in nitrogen atmosphere was charged with 250 g of methyl ethyl ketone, which was heated at 80° C. with stirring. With stirring, the monomer solution was added dropwise to the flask over 4 hours. After the completion of dropwise addition, the polymerization solution was continuously stirred for 4 hours while maintaining its temperature at 80° C. The polymerization solution was cooled to room temperature, whereupon it was added dropwise to 10 kg of hexane/diisopropyl ether solution. The precipitate was collected by filtration, washed twice with 5 kg of hexane, and vacuum dried at 50° C. for 20 hours, obtaining a copolymer in white powder solid form. Under acidic conditions, 100 g of the polymer was reacted with 40.5 g of 2-methyl-1-propenyl methyl ether. This was followed by neutralization, phase separation, and crystallization, obtaining 128 g of a polymer, designated Polymer 4.

Synthesis Example 2-5

Synthesis of Polymer 5

Polymer 5 was synthesized by the same procedure as in Synthesis Example 2-4 aside from using 2-methyl-1-propenyl 8-tricyclo[5.2.1.0$^{2,6}$]decanyl ether instead of 2-methyl-1-propenyl methyl ether.

Synthesis Example 2-6

Synthesis of Polymer 6

Polymer 6 was synthesized by the same procedure as in Synthesis Example 2-4 aside from using 2-methyl-1-propenyl 2-adamantyl ether instead of 2-methyl-1-propenyl methyl ether.

Synthesis Examples 2-7 to 2-12

Synthesis of Polymers 7 to 12

Polymers containing hydroxystyrene units in Table 1 were synthesized by the same procedure as in Synthesis Example 2-1, 2-2 or 2-3 aside from changing the type and amount of monomers. Polymers containing 4-hydroxyphenyl methacrylate units in Table 1 were synthesized by the same procedure as in Synthesis Example 2-4, 2-5 or 2-6 aside from changing the type and amount of monomers.

Synthesis Example 2-13

Synthesis of Polymer 13

In nitrogen atmosphere, 42.4 g of 4-hydroxyphenyl methacrylate, 40.6 g of 5-oxo-4-oxatricyclo[4.2.1.0$^{3,7}$]nonan-2-yl methacrylate, 16.9 g of 1-methoxy-2-methyl-1-propyl methacrylate, 9.3 g of dimethyl 2,2'-azobis(2-methylpropionate) (V-601 by Wako Pure Chemical Industries, Ltd.), and 124 g of methyl ethyl ketone were fed into a dropping cylinder to form a monomer solution. A flask in nitrogen atmosphere was charged with 62 g of methyl ethyl ketone, which was heated at 80° C. with stirring. With stirring, the monomer solution was added dropwise to the flask over 4 hours. After the completion of dropwise addition, the polymerization solution was continuously stirred for 4 hours while maintaining its temperature at 80° C. The polymerization solution was cooled to room temperature, whereupon it was added dropwise to 1.5 kg of hexane/diisopropyl ether solution. The precipitate was collected by filtration, washed twice with 300 g of hexane, and vacuum dried at 50° C. for 20 hours, obtaining a copolymer in white powder solid form. It is designated Polymer 13.

Synthesis Examples 2-14 to 2-16

Synthesis of Polymers 14 to 16

Polymers in Table 1 were synthesized by the same procedure as in Synthesis Example 2-13 aside from changing the type and amount of monomers.

Table 1 shows the proportion (in molar ratio) of units incorporated in these polymers, and Tables 2 to 4 show the structure of recurring units.

TABLE 1
| | Unit 1 | Proportion (mol %) | Unit 2 | Proportion (mol %) | Unit 3 | Proportion (mol %) |
|---|---|---|---|---|---|---|
| Polymer 1 | A-1 | 70.0 | B-1 | 20.0 | C-1 | 10.0 |
| Polymer 2 | A-1 | 78.0 | B-3 | 12.0 | C-1 | 10.0 |
| Polymer 3 | A-1 | 79.0 | B-5 | 11.0 | C-1 | 10.0 |
| Polymer 4 | A-2 | 67.0 | B-2 | 23.0 | C-1 | 10.0 |
| Polymer 5 | A-2 | 76.0 | B-4 | 14.0 | C-1 | 10.0 |
| Polymer 6 | A-2 | 77.0 | B-6 | 13.0 | C-1 | 10.0 |
| Polymer 7 | A-1 | 68.0 | B-1 | 22.0 | C-2 | 10.0 |
| Polymer 8 | A-1 | 76.0 | B-3 | 14.0 | C-2 | 10.0 |
| Polymer 9 | A-1 | 77.0 | B-5 | 13.0 | C-2 | 10.0 |
| Polymer 10 | A-2 | 64.0 | B-2 | 26.0 | C-2 | 10.0 |
| Polymer 11 | A-2 | 73.0 | B-4 | 17.0 | C-2 | 10.0 |
| Polymer 12 | A-2 | 74.0 | B-6 | 16.0 | C-2 | 10.0 |
| Polymer 13 | A-2 | 46.0 | B-7 | 19.0 | C-3 | 35.0 |
| Polymer 14 | A-2 | 50.0 | B-8 | 15.0 | C-3 | 35.0 |
| Polymer 15 | A-2 | 50.0 | B-9 | 15.0 | C-3 | 35.0 |
| Polymer 16 | A-1 | 67.0 | B-10 | 23.0 | C-1 | 10.0 |
TABLE 2
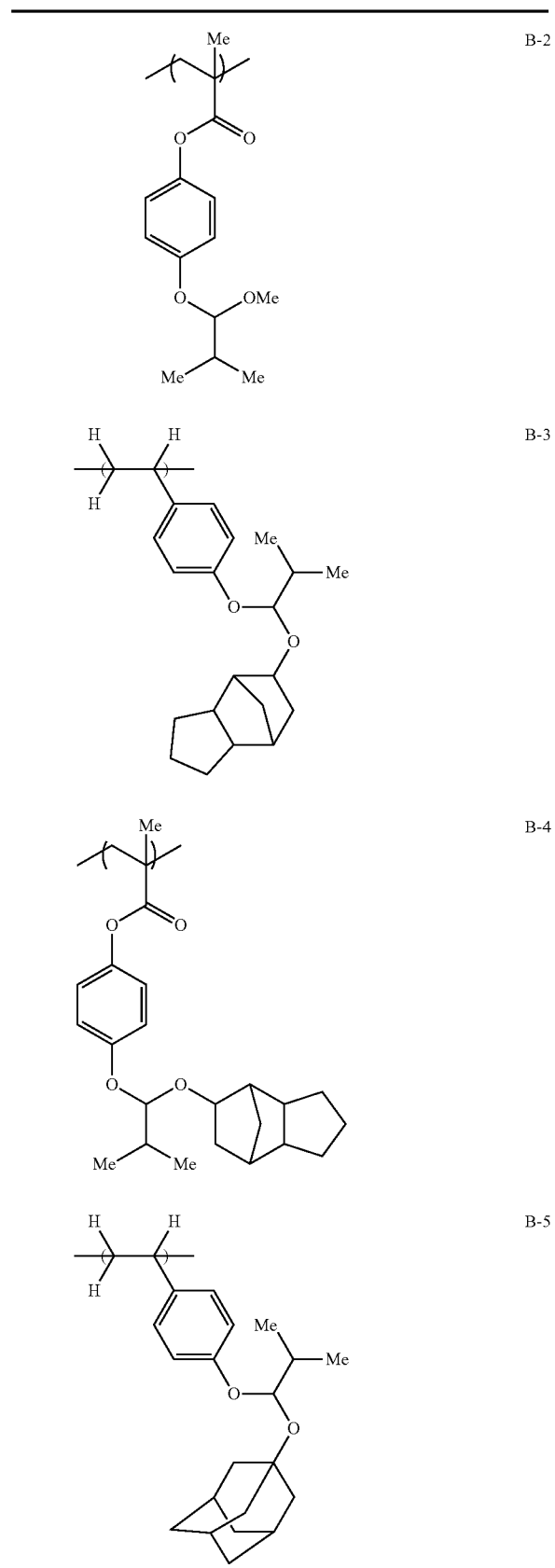

TABLE 3-continued

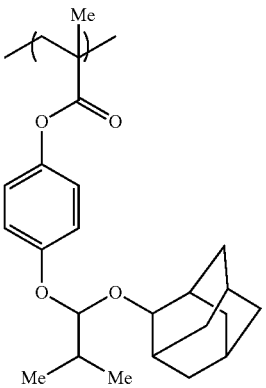
B-6

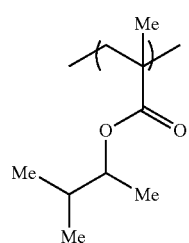
B-7

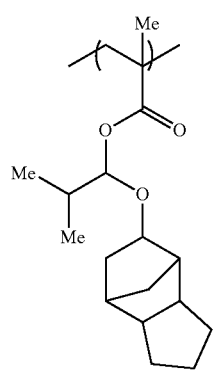
B-8

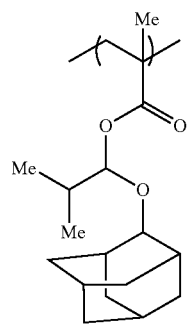
B-9

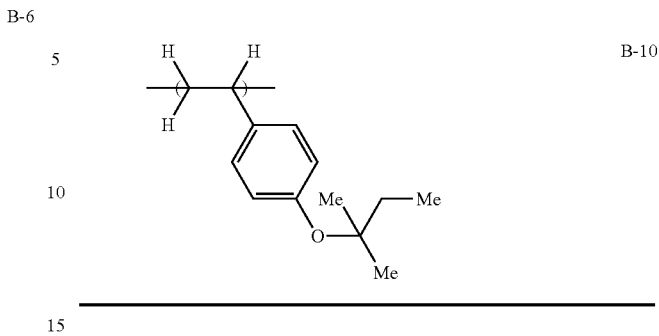
B-10

TABLE 4

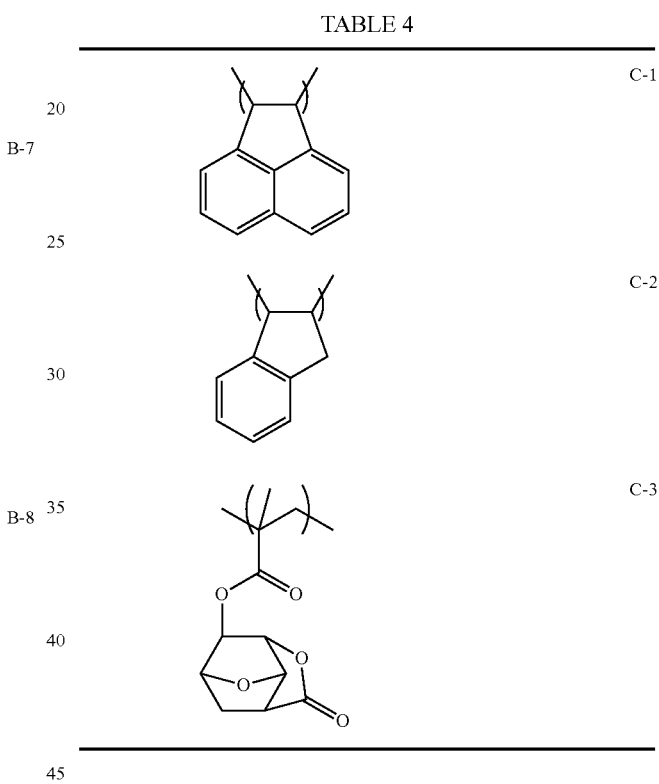

C-1

C-2

C-3

Preparation of Positive Resist Composition

A positive resist composition in solution form was prepared by dissolving each polymer (Polymers 1 to 16 synthesized above), a photoacid generator and basic compound in an organic solvent in accordance with the recipe shown in Table 6, and filtering through a filter with a pore size of 0.2 μm or a nylon or UPE filter with a pore size of 0.02 μm. The basic compound used is Base-1 of the structure shown below. The photoacid generator used is of the structure shown in Table 5.

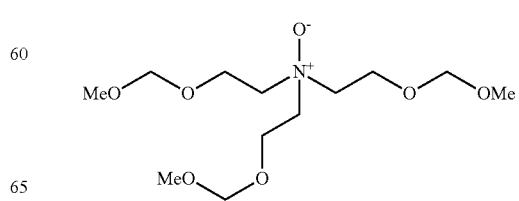
(Base-1)

TABLE 5
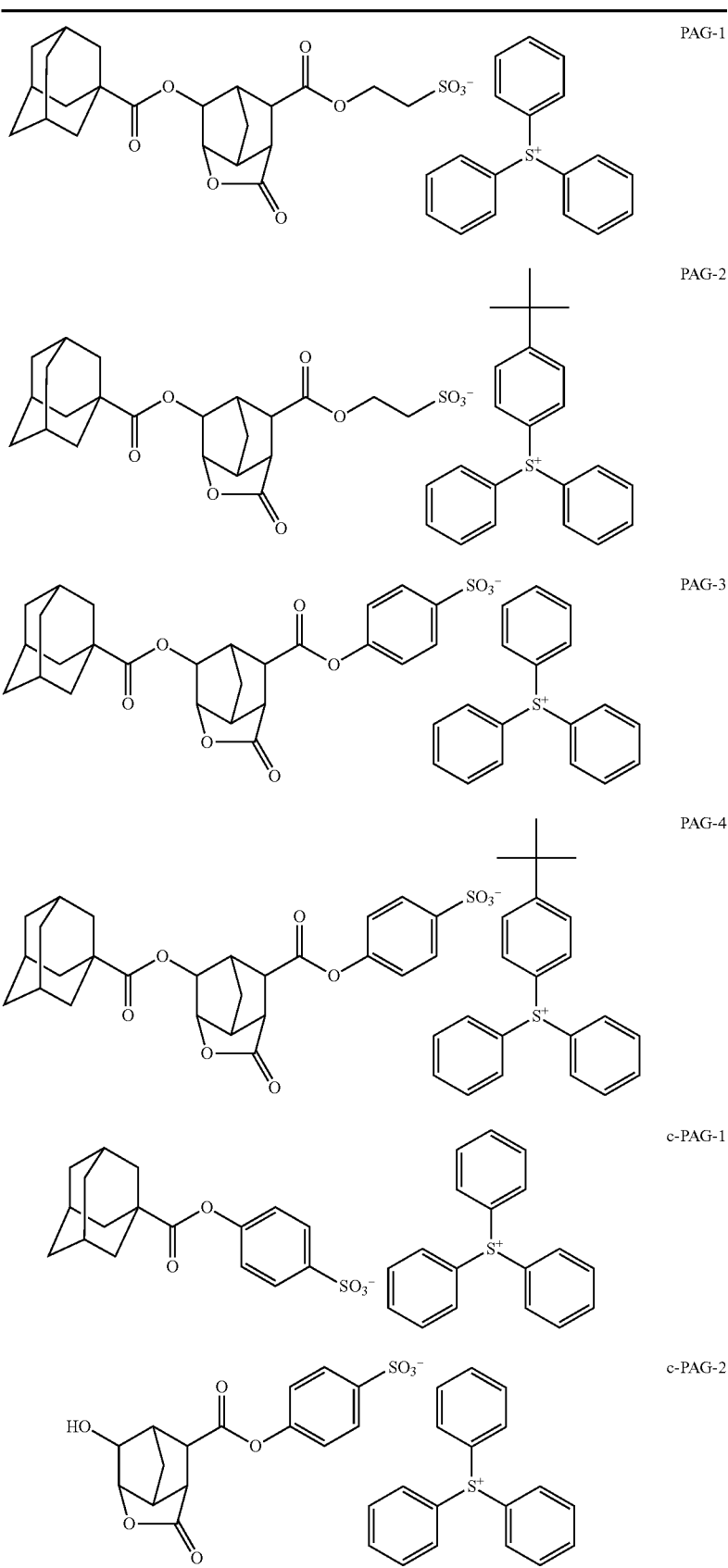

TABLE 5-continued c-PAG-3

[Chemical structure: mesitylene sulfonate anion with triphenylsulfonium cation]

The organic solvents used are PGMEA (propylene glycol monomethyl ether acetate), EL (ethyl lactate), PGME (propylene glycol monomethyl ether), and CyH (cyclohexanone). The composition contained 0.075 part of surfactant PF-636 (Omnova Solutions Inc.).

tem Nanospec (Nanometrics Inc.). Measurement was made at 81 points in the plane of the blank substrate excluding a peripheral band extending 10 mm inward from the blank periphery, and an average film thickness and a film thickness range were computed therefrom.

TABLE 6

|  |  | Photoacid generator 1 (pbw) | Photoacid generator 2 (pbw) | Resin (pbw) | Base (pbw) | Solvent 1 (pbw) | Solvent 2 (pbw) | Solvent 3 (pbw) |
|---|---|---|---|---|---|---|---|---|
| Example | 1 | PAG-3(8) |  | Polymer 1(80) | Base-1(0.97) | PGMEA(1,000) | EL(1,000) | PGME(1,300) |
|  | 2 | PAG-3(8) |  | Polymer 2(80) | Base-1(0.97) | PGMEA(1,000) | EL(1,000) | PGME(1,300) |
|  | 3 | PAG-3(8) |  | Polymer 3(80) | Base-1(0.97) | PGMEA(1,000) | EL(1,000) | PGME(1,300) |
|  | 4 | PAG-3(8) |  | Polymer 4(80) | Base-1(0.97) | PGMEA(1,000) | EL(1,000) | PGME(1,300) |
|  | 5 | PAG-3(8) |  | Polymer 5(80) | Base-1(0.97) | PGMEA(1,000) | EL(1,000) | PGME(1,300) |
|  | 6 | PAG-3(8) |  | Polymer 6(80) | Base-1(0.97) | PGMEA(1,000) | EL(1,000) | PGME(1,300) |
|  | 7 | PAG-3(8) |  | Polymer 7(80) | Base-1(0.97) | PGMEA(1,000) | EL(1,000) | PGME(1,300) |
|  | 8 | PAG-3(8) |  | Polymer 8(80) | Base-1(0.97) | PGMEA(1,000) | EL(1,000) | PGME(1,300) |
|  | 9 | PAG-3(8) |  | Polymer 9(80) | Base-1(0.97) | PGMEA(1,000) | EL(1,000) | PGME(1,300) |
|  | 10 | PAG-3(8) |  | Polymer 10(80) | Base-1(0.97) | PGMEA(1,000) | EL(1,000) | PGME(1,300) |
|  | 11 | PAG-3(8) |  | Polymer 11(80) | Base-1(0.97) | PGMEA(1,000) | EL(1,000) | PGME(1,300) |
|  | 12 | PAG-3(8) |  | Polymer 12(80) | Base-1(0.97) | PGMEA(1,000) | EL(1,000) | PGME(1,300) |
|  | 13 | PAG-1(8) |  | Polymer 2(80) | Base-1(0.97) | PGMEA(1,000) | EL(1,000) | PGME(1,300) |
|  | 14 | PAG-1(8) |  | Polymer 3(80) | Base-1(0.97) | PGMEA(1,000) | EL(1,000) | PGME(1,300) |
|  | 15 | PAG-1(4) | PAG-2(4) | Polymer 2(80) | Base-1(0.97) | PGMEA(1,000) | EL(1,000) | PGME(1,300) |
|  | 16 | PAG-1(4) | PAG-2(4) | Polymer 3(80) | Base-1(0.97) | PGMEA(1,000) | EL(1,000) | PGME(1,300) |
|  | 17 | PAG-3(4) | PAG-4(4) | Polymer 2(80) | Base-1(0.97) | PGMEA(1,000) | EL(1,000) | PGME(1,300) |
|  | 18 | PAG-3(4) | PAG-4(4) | Polymer 3(80) | Base-1(0.97) | PGMEA(1,000) | EL(1,000) | PGME(1,300) |
|  | 19 | PAG-1(8) |  | Polymer 8(80) | Base-1(0.97) | PGMEA(1,000) | EL(1,000) | PGME(1,300) |
|  | 20 | PAG-1(8) |  | Polymer 9(80) | Base-1(0.97) | PGMEA(1,000) | EL(1,000) | PGME(1,300) |
|  | 21 | PAG-1(4) | PAG-2(4) | Polymer 8(80) | Base-1(0.97) | PGMEA(1,000) | EL(1,000) | PGME(1,300) |
|  | 22 | PAG-1(4) | PAG-2(4) | Polymer 9(80) | Base-1(0.97) | PGMEA(1,000) | EL(1,000) | PGME(1,300) |
|  | 23 | PAG-3(4) | PAG-4(4) | Polymer 8(80) | Base-1(0.97) | PGMEA(1,000) | EL(1,000) | PGME(1,300) |
|  | 24 | PAG-3(4) | PAG-4(4) | Polymer 9(80) | Base-1(0.97) | PGMEA(1,000) | EL(1,000) | PGME(1,300) |
|  | 25 | PAG-1(8) |  | Polymer 13(80) | Base-1(0.97) | PGMEA(800) | CyH(1,600) | PGME(400) |
|  | 26 | PAG-1(8) |  | Polymer 14(80) | Base-1(0.97) | PGMEA(800) | CyH(1,600) | PGME(400) |
|  | 27 | PAG-1(8) |  | Polymer 15(80) | Base-1(0.97) | PGMEA(800) | CyH(1,600) | PGME(400) |
|  | 28 | PAG-3(8) |  | Polymer 16(80) | Base-1(0.97) | PGMEA(1,000) | EL(1,000) | PGME(1,300) |
| Comparative Example | 1 | c-PAG-1(8) |  | Polymer 2(80) | Base-1(0.97) | PGMEA(1,000) | EL(1,000) | PGME(1,300) |
|  | 2 | c-PAG-1(8) |  | Polymer 3(80) | Base-1(0.97) | PGMEA(1,000) | EL(1,000) | PGME(1,300) |
|  | 3 | c-PAG-2(8) |  | Polymer 2(80) | Base-1(0.97) | PGMEA(1,000) | EL(1,000) | PGME(1,300) |
|  | 4 | c-PAG-2(8) |  | Polymer 3(80) | Base-1(0.97) | PGMEA(1,000) | EL(1,000) | PGME(1,300) |
|  | 5 | c-PAG-3(8) |  | Polymer 2(80) | Base-1(0.97) | PGMEA(1,000) | EL(1,000) | PGME(1,300) |
|  | 6 | c-PAG-3(8) |  | Polymer 3(80) | Base-1(0.97) | PGMEA(1,000) | EL(1,000) | PGME(1,300) |
|  | 7 | c-PAG-1(8) |  | Polymer 13(80) | Base-1(0.97) | PGMEA(800) | CyH(1,600) | PGME(400) |

Examples 1 to 24, 28 and Comparative Examples 1 to 6

EB Writing Test

Using a coater/developer system ACT-M (Tokyo Electron Ltd.), each of the positive resist compositions (prepared above as Examples 1 to 24, 28 and Comparative Examples 1 to 6) was spin coated onto a mask blank of 152 mm squares having a chromium oxynitride film at the outermost surface and prebaked on a hot plate at 90° C. for 600 seconds to form a resist film of 90 nm thick. The thickness of the resist film was measured by an optical film thickness measurement sys- The coated mask blanks were exposed to electron beam using an EB writer system EBM-5000Plus (NuFlare Technology Inc., accelerating voltage 50 keV), then baked (PEB) at 120° C. for 600 seconds, and developed in a 2.38 wt % tetramethylammonium hydroxide (TMAH) aqueous solution, thereby yielding positive patterns.

The patterned mask blank was observed under a top-down scanning electron microscope (TDSEM). The optimum exposure (Eop) was defined as the exposure dose ($\mu C/cm^2$) which provided a 1:1 resolution at the top and bottom of a 400-nm 1:1 line-and-space pattern. The maximum resolution of the resist was defined as the minimum line width of a line-and-space pattern that could be resolved at the optimum exposure.

The LER of a 200-nm line-and-space pattern was measured under SEM. On observation in cross section of the resist pattern under SEM, it was visually judged whether or not the pattern profile was rectangular. With respect to adhesion, any peel was visually inspected during observation under TDSEM. Table 7 tabulates the test results of the inventive and comparative resist compositions on EB image writing.

The post-exposure delay (PED) in vacuum was evaluated by exposing the coated blank on the EB writer system as above, holding it in the vacuum system for 20 hours, thereafter effecting PEB and development. The line width of the 400-nm line-and-space pattern at Eop was measured and compared with the line width of the pattern baked immediately after exposure, with a difference ΔCD (nm) reported.

For evaluation of CDU, the line width of the pattern at the optimum exposure Eop (μC/cm$^2$) (which provided a 1:1 resolution of a 400-nm 1:1 line-and-space pattern) was measured at 49 points in the plane of the blank substrate excluding a peripheral band extending 20 mm inward from the blank periphery. A 3σ value was computed by subtracting the width at each measurement point from the average line width, and reported as CDU.

TABLE 7

|  |  | Eop, μC/cm$^2$ | Maximum resolution, nm | LER, nm | PED (ΔCD), nm | CDU (3σ), nm | Pattern profile |
|---|---|---|---|---|---|---|---|
| Example | 1 | 21 | 45 | 4.7 | 2.5 | 2.2 | rectangular |
|  | 2 | 22 | 40 | 4.6 | 2.2 | 2.3 | rectangular |
|  | 3 | 24 | 40 | 4.6 | 2.1 | 2.2 | rectangular |
|  | 4 | 23 | 45 | 4.6 | 2.4 | 2.1 | rectangular |
|  | 5 | 25 | 45 | 4.9 | 2.6 | 2.3 | rectangular |
|  | 6 | 24 | 45 | 4.4 | 2.6 | 2.2 | rectangular |
|  | 7 | 23 | 45 | 5.0 | 2.5 | 2.2 | rectangular |
|  | 8 | 23 | 45 | 4.7 | 2.6 | 2.4 | rectangular |
|  | 9 | 25 | 45 | 4.6 | 2.6 | 2.2 | rectangular |
|  | 10 | 22 | 45 | 4.8 | 2.5 | 2.2 | rectangular |
|  | 11 | 23 | 45 | 4.8 | 2.6 | 2.3 | rectangular |
|  | 12 | 21 | 45 | 4.7 | 2.7 | 2.1 | rectangular |
|  | 13 | 24 | 40 | 4.6 | 2.3 | 2.2 | rectangular |
|  | 14 | 25 | 40 | 4.8 | 2.2 | 2.2 | rectangular |
|  | 15 | 23 | 40 | 4.7 | 2.2 | 2.3 | rectangular |
|  | 16 | 22 | 40 | 4.8 | 2.3 | 2.4 | rectangular |
|  | 17 | 21 | 40 | 4.5 | 2.3 | 2.2 | rectangular |
|  | 18 | 21 | 40 | 4.6 | 2.2 | 2.3 | rectangular |
|  | 19 | 24 | 45 | 4.6 | 2.4 | 2.5 | rectangular |
|  | 20 | 25 | 45 | 4.8 | 2.3 | 2.4 | rectangular |
|  | 21 | 23 | 40 | 4.9 | 2.5 | 2.3 | rectangular |
|  | 22 | 24 | 40 | 4.8 | 2.2 | 2.2 | rectangular |
|  | 23 | 25 | 45 | 4.8 | 2.5 | 2.3 | rectangular |
|  | 24 | 24 | 45 | 4.8 | 2.4 | 2.2 | rectangular |
|  | 28 | 24 | 45 | 5.0 | 2.8 | 2.6 | rectangular |
| Comparative Example | 1 | 24 | 55 | 7.2 | 3.7 | 3.4 | rectangular |
|  | 2 | 23 | 55 | 6.9 | 3.6 | 3.5 | rectangular |
|  | 3 | 25 | 55 | 8.3 | 3.7 | 3.6 | rectangular |
|  | 4 | 26 | 55 | 8.4 | 3.6 | 3.6 | rectangular |
|  | 5 | 25 | 55 | 7.6 | 3.7 | 3.5 | rectangular |
|  | 6 | 22 | 55 | 7.8 | 3.7 | 3.6 | rectangular |

Examples 25 to 27 and Comparative Example 7

EUV Exposure Test

Each of the positive resist compositions (prepared above as Examples 25 to 27 and Comparative Example 7) was spin coated on a silicon substrate (diameter 4 inches, vapor primed with hexamethyldisilazane (HMDS)) and prebaked on a hot plate at 105° C. for 60 seconds to form a resist film of 50 nm thick. EUV exposure was performed by dipole illumination at NA 0.3.

Immediately after the exposure, the resist film was baked (PEB) on a hot plate for 60 seconds and puddle developed in a 2.38 wt % TMAH aqueous solution for 30 seconds to form a positive pattern.

The optimum exposure (Eop) is defined as the exposure dose that provides a 1:1 resolution of a 35-nm line-and-space pattern. Maximum resolution is a minimum size that can be resolved at Eop. The 35-nm line-and-space pattern was measured for LER under SEM. On observation in cross section of the resist pattern under SEM, it was visually judged whether or not the pattern profile was rectangular. With respect to adhesion, any peel was visually inspected during observation under TDSEM.

The results of the resist compositions by EUV lithography test is shown in Table 8.

TABLE 8

|  |  | Eop, μC/cm$^2$ | Maximum resolution, nm | LER, nm | Pattern profile |
|---|---|---|---|---|---|
| Example | 25 | 15 | 28 | 4.0 | rectangular |
|  | 26 | 14 | 26 | 4.1 | rectangular |
|  | 27 | 15 | 28 | 4.1 | rectangular |
| Comparative Example | 7 | 12 | 50 | 9.6 | rectangular |

As seen from the results in Tables 7 and 8, the resist compositions containing the sulfonium salt of formula (1) within the scope of the invention (Examples 1 to 24 or Examples 25 to 27) exhibit a high resolution, satisfactory pattern rectangularity, and acceptable values of CDU, LER and PED performance. In contrast, the resist compositions containing a sulfonium salt which is less bulky than the sulfonium salt of formula (1) (Comparative Examples 1 to 6 or Comparative Example 7) are inferior in resolution, CDU, LER and PED performance. This is because the sulfonium salts used in Comparative Examples are less bulky than the sulfonium salts of formula (1) and fail in effective control of acid diffusion.

It has been demonstrated that using the resist composition within the scope of the invention, a pattern having CDU, minimal PED impact and minimal LER can be formed via exposure. The pattern forming process using the resist composition within the scope of the invention is advantageous in the photolithography for semiconductor device fabrication and photomask blank processing.

While the invention has been illustrated and described in typical embodiments, it is not intended to be limited to the details shown. Any modified embodiments having substantially the same features and achieving substantially the same results as the technical idea disclosed herein are within the spirit and scope of the invention.

Japanese Patent Application No. 2013-261348 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the general formula (1):

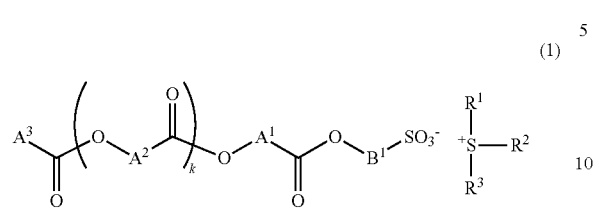

wherein $A^1$ is a straight, branched or cyclic, $C_1$-$C_{10}$ divalent hydrocarbon group which may be substituted with a heteroatom or separated by a heteroatom, $A^2$ is a straight, branched or cyclic, $C_1$-$C_{10}$ divalent hydrocarbon group, $A^3$ is selected from the group consisting of those having the following formulae:

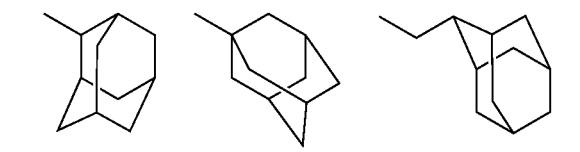
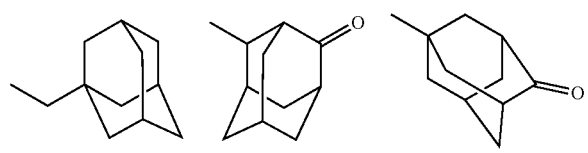
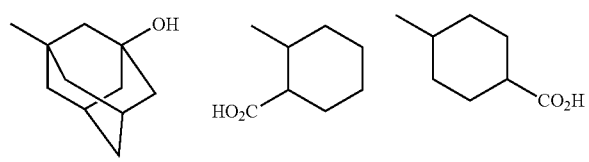
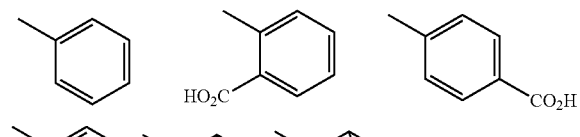
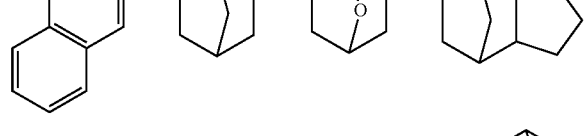
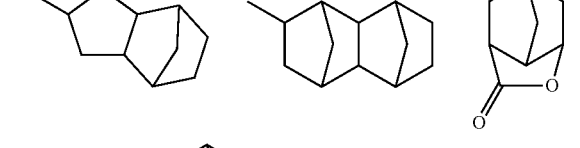
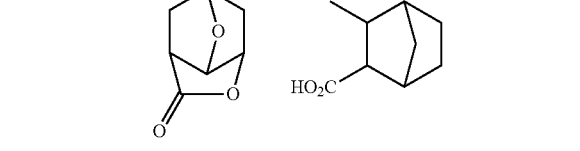

-continued

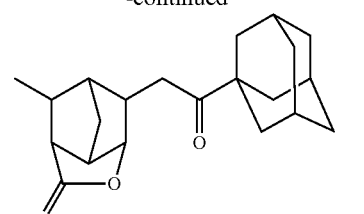
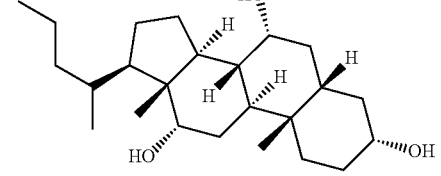
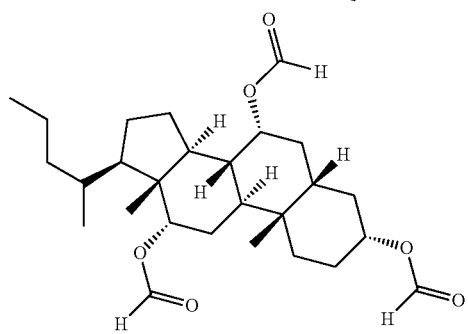
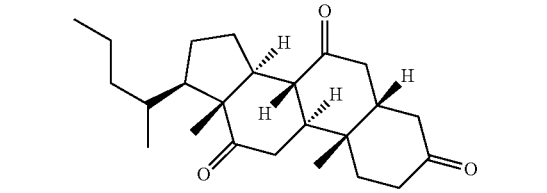
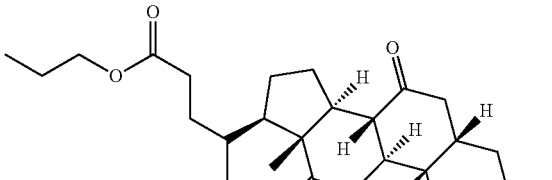
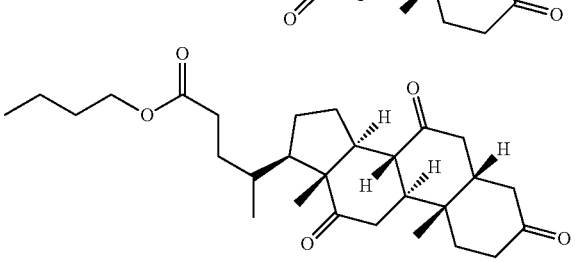

wherein the broken line denotes a valence bond, $B^1$ is a $C_i$-$C_{io}$ alkylene group or $C_6$-$C_{18}$ arylene group which may contain an ethereal oxygen atom, k is 0 or 1, $R^1$, $R^2$ and $R^3$ are each independently a substituted or unsubstituted, straight or branched $C_1$-$C_{10}$ alkyl, alkenyl or oxoalkyl group, or a substituted or unsubstituted $C_6$-$C_{18}$ aryl, aralkyl or aryloxoalkyl group, or any two or more of $R^1$, $R^2$ and $R^3$ may bond together to form a ring with the sulfur atom.

2. The sulfonium salt of claim 1 wherein $A^1$ is a group having the general formula (2):

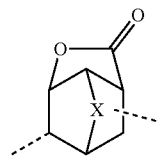

wherein X is O or $CH_2$, and the broken line denotes a valence bond.

3. A resist composition comprising the sulfonium salt of claim 1.

4. The resist composition of claim 3, further comprising a resin adapted to be decomposed under the action of acid to increase its solubility in alkaline developer.

5. The resist composition of claim 4 wherein the resin is a polymer comprising recurring units having the general formula (4):

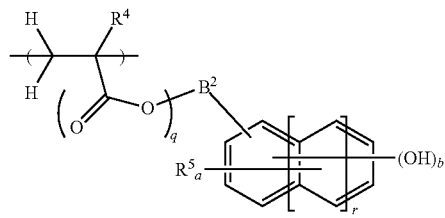

wherein q is 0 or 1, r is an integer of 0 to 2, $R^4$ is hydrogen, fluorine, methyl or trifluoromethyl, $R^5$ is each independently hydrogen or $C_1$-$C_6$ alkyl group, $B^2$ is a single bond or a $C_1$-$C_{10}$ alkylene group which may contain an ether bond, a is an integer satisfying $a \leq 5+2r-b$, and b is an integer of 1 to 3.

6. The resist composition of claim 5 wherein the polymer further comprises as an acid labile group-protected unit which turns alkali soluble under the action of acid, recurring units having the general formula (5):

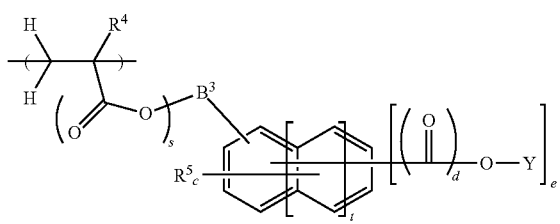

wherein s is 0 or 1, t is an integer of 0 to 2, $R^4$ and $R^5$ are as defined above, $B^3$ is a single bond or a $C_1$-$C_{10}$ alkylene group which may contain an ether bond, c is an integer satisfying $c \leq 5+2t-e$, d is 0 or 1, e is an integer of 1 to 3, Y is an acid labile group when e =1, Y is hydrogen or an acid labile group when e =2 or 3, with at least one Y being an acid labile group.

7. The resist composition of claim 5 wherein the polymer further comprises recurring units having the general formula (6) and/or (7):

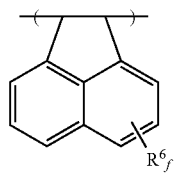

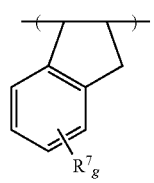

wherein f is an integer of 0 to 6, $R^6$ is each independently hydrogen, an optionally halo-substituted $C_1$-$C_6$ alkyl or primary or secondary alkoxy group, or optionally halo-substituted $C_1$-$C_7$ alkylcarbonyloxy group, g is an integer of 0 to 4, and $R^7$ is each independently hydrogen, an optionally halo-substituted $C_1$-$C_6$ alkyl or primary or secondary alkoxy group, or optionally halo-substituted $C_1$-$C_7$ alkylcarbonyloxy group.

8. A pattern forming process comprising the steps of applying the resist composition of claim 3 onto a processable substrate to form a resist film, exposing the resist film to high-energy radiation, and developing in an alkaline developer to form a resist pattern.

9. The process of claim 8 wherein the high-energy radiation is EUV or EB.

10. The process of claim 8 wherein the processable substrate has an outermost surface made of a chromium-containing material.

11. The process of claim 8 wherein the processable substrate is a photomask blank.

* * * * *